United States Patent
Chen et al.

(10) Patent No.: US 6,609,408 B2
(45) Date of Patent: Aug. 26, 2003

(54) METHOD FOR SELECTING A COVER MATERIAL FOR USE WITH A VEHICLE SEAT

(75) Inventors: Pusheng Chen, Novi, MI (US); Ivana Vucelic, Wixom, MI (US); Donald C. Thompson, Wixom, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 09/858,689

(22) Filed: May 16, 2001

(65) Prior Publication Data

US 2003/0047013 A1 Mar. 13, 2003

(51) Int. Cl.[7] .............................................. G01N 19/00
(52) U.S. Cl. .................................. 73/7; 73/866; 702/34
(58) Field of Search ........................... 73/7, 159, 866, 73/849, 852, 865.8; 702/34

(56) References Cited

U.S. PATENT DOCUMENTS

| | | | |
|---|---|---|---|
| 3,763,483 A | * 10/1973 | Urmenyi | 73/159 |
| 4,317,301 A | 3/1982 | Timphony et al. | |
| 4,343,103 A | 8/1982 | Murashima | |
| 4,526,420 A | 7/1985 | Kawamura et al. | |
| 4,541,885 A | 9/1985 | Caudill, Jr. | |
| 4,845,925 A | 7/1989 | Thompson | |
| 4,952,062 A | * 8/1990 | Bean, III et al. | 356/43 |
| 4,995,178 A | 2/1991 | Randolph | |
| 5,209,084 A | 5/1993 | Robinson et al. | |
| 5,326,150 A | 7/1994 | Robinson et al. | |
| 5,347,732 A | 9/1994 | Padawer | |
| 5,408,770 A | 4/1995 | Suzuki | |
| 5,529,373 A | 6/1996 | Olson et al. | |
| 6,199,246 B1 | 3/2001 | Cibin et al. | |
| 6,260,924 B1 | 7/2001 | Jones et al. | |

FOREIGN PATENT DOCUMENTS

| | | | | |
|---|---|---|---|---|
| JP | 187209 | * | 10/1984 | 73/622 |
| JP | 447 | * | 1/1989 | 73/159 |
| JP | 3255946 | * | 11/1991 | |

OTHER PUBLICATIONS

U.S. patent application Ser. No. 09/858,737 filed May 16, 2001, Chen et al.

* cited by examiner

Primary Examiner—Helen Kwok
Assistant Examiner—Nashmiya Fayyaz
(74) Attorney, Agent, or Firm—Bill C. Panagos

(57) ABSTRACT

A method for selecting a cover material for use with a vehicle seat component includes establishing a material processability standard for cover materials selected from the group consisting of standards for marking resistance, fabric pattern, pile bind, rippling resistance, laminate wrinkle resistance, raveling resistance, seam puckering, stretch, and elongation; conducting testing of a cover material for compliance with the material processability standard to determine whether the cover material meets requirements of the material processability standard; and considering test results of the cover material before proceeding to utilize the cover material in manufacturing of the vehicle seat component.

54 Claims, 13 Drawing Sheets

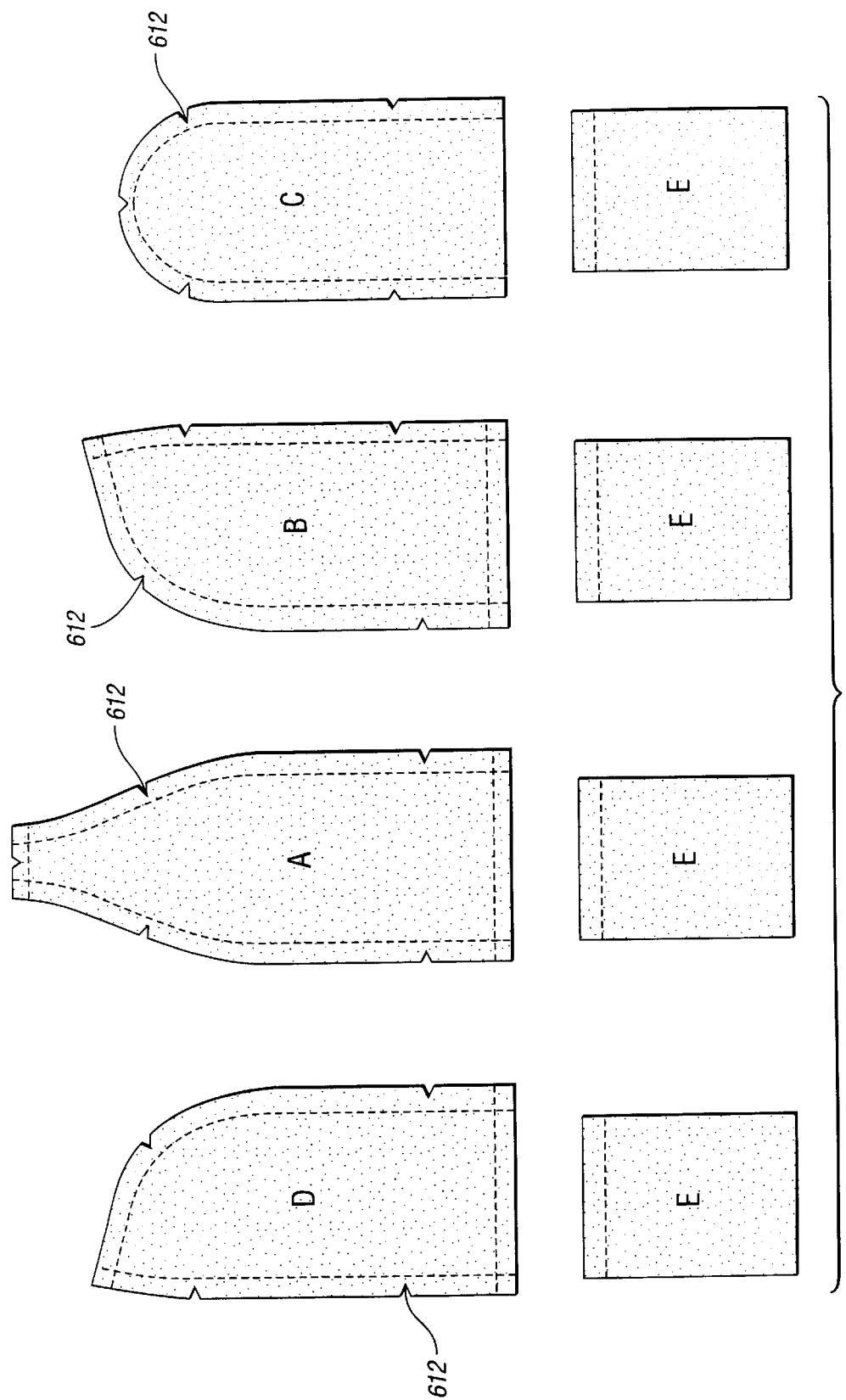

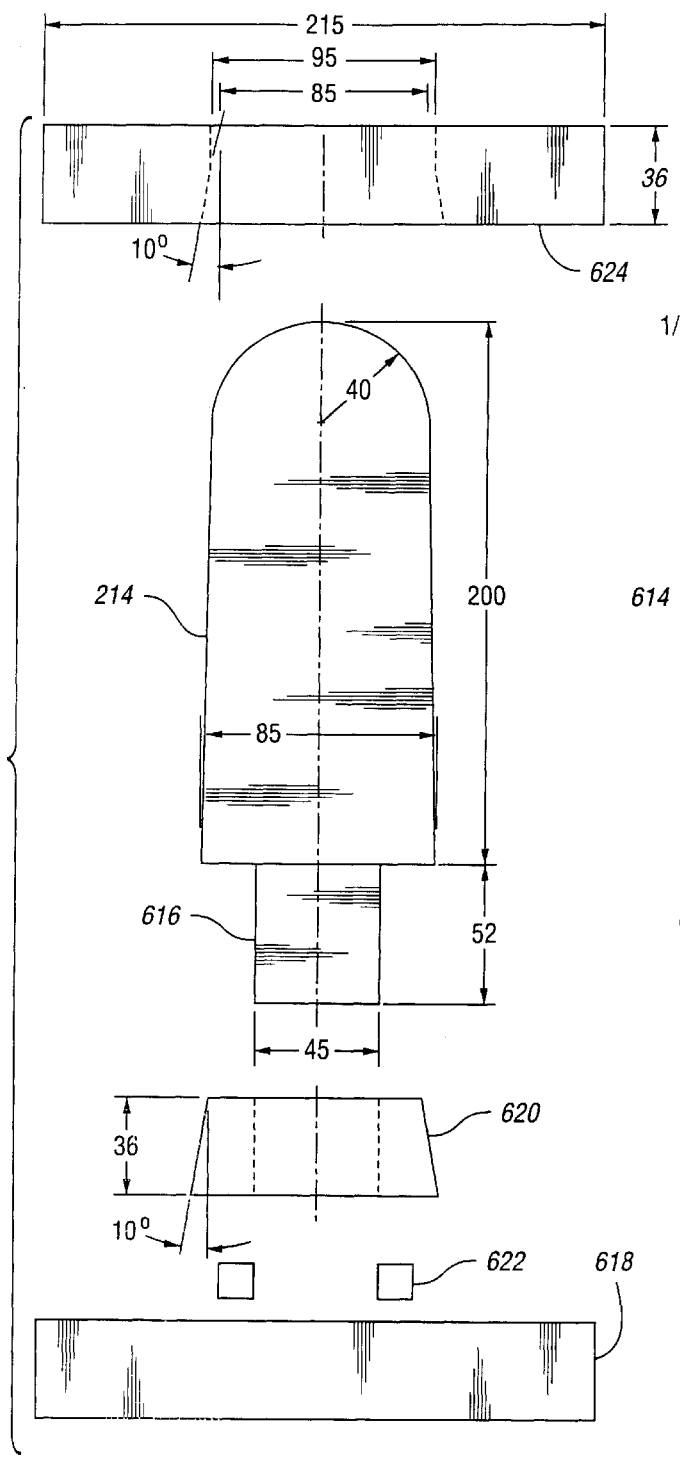
*Fig. 20*
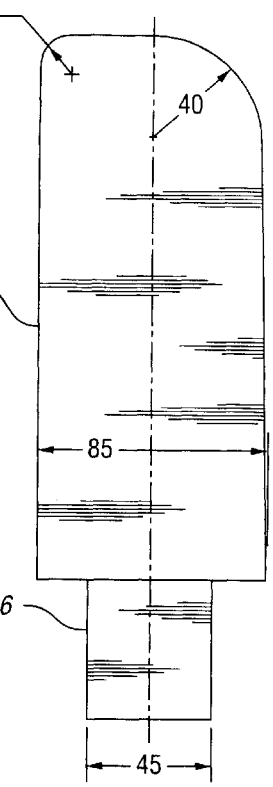
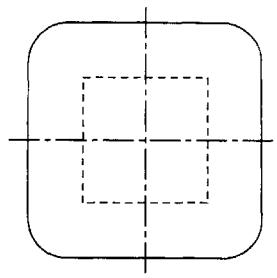
*Fig. 19*        *Fig. 21*

METHOD FOR SELECTING A COVER MATERIAL FOR USE WITH A VEHICLE SEAT

BACKGROUND OF THE INVENTION

1. Field of the Invention

The invention relates to a method for selecting a cover material for use with a vehicle seat component.

2. Background Art

Vehicle seats for use with a motor vehicle typically include a foam core covered by a seat cover. The seat cover may include an outer layer made of such materials as fabric, vinyl, or leather, and one or more other layers, such as a foam pad and/or a scrim layer attached to the outer layer. Furthermore, the seat cover may be divided into a number of panels that are sewn together, or otherwise joined together, to form a desired shape.

Frequently, the materials to be used for the seat cover are selected at an early stage in the vehicle seat development process. For example, such materials may be selected prior to determination of the final contour of the vehicle seat. As a result, processability issues related to the seat cover may arise during the vehicle seat manufacturing process. For example, it may be discovered that the materials selected for the seat cover are not able to conform to the final contour of the vehicle seat without excessively wrinkling. As another example, it may be discovered that the materials selected for the seat cover tend to pucker at or near seam locations.

SUMMARY OF THE INVENTION

The present invention provides a method for selecting a cover material for use with a vehicle seat component and the method includes determining the processability of the cover material before proceeding to utilize the cover material in manufacturing of the vehicle seat component. As a result, a sufficiently processable cover material may be effectively selected for a particular vehicle seat application.

Under the invention, a method for selecting a cover material for use with a vehicle seat component includes establishing a material processability standard for cover materials selected from the group consisting of standards for marking resistance, fabric pattern, pile bind, rippling resistance, laminate wrinkle resistance, raveling resistance, seam puckering, stretch, and elongation; conducting testing of a cover material for compliance with the material processability standard to determine whether the cover material meets requirements of the material processability standard; and considering test results of the cover material before proceeding to utilize the cover material in manufacturing of the vehicle seat component.

The step of considering test results may include conferring with a vehicle manufacturer regarding the test results when the cover material does not meet the requirements of the material processability standard. As a result, all interested parties may be involved in selecting a suitable cover material.

In addition, the method may involve establishing two or more material processability standards selected from the standards identified above; conducting testing of the cover material for compliance with the material processability standards to determine whether the cover material meets requirements of the material processability standards; and considering test results of the cover material before proceeding to utilize the cover material in manufacturing of the vehicle seat component.

Further under the invention, a method for determining usability of a cover material with a vehicle seat component includes conducting testing of the cover material for compliance with a material processability standard selected from the group consisting of standards for marking resistance, fabric pattern, pile bind, rippling resistance, laminate wrinkle resistance, raveling resistance, seam puckering, stretch, and elongation to determine whether the cover material meets requirements of the material processability standard before proceeding to utilize the cover material in manufacturing of the vehicle seat component.

These and other objects, features and advantages of the invention are readily apparent from the following detailed description of the preferred embodiments for carrying out the invention when taken in conjunction with the accompanying drawings.

BRIEF DESCRIPTION OF THE DRAWINGS

FIG. 18 is a front view of multiple panels that are used to form the cover shown in FIG. 17;

FIG. 19 is an exploded front view of the apparatus of FIG. 17 showing a form, an inner wedge ring, an outer wedge ring, a base for supporting the form and the rings, and spacers for spacing the inner wedge ring away from the base;

FIG. 20 is a side view of the form;

FIG. 21 is a top view of the form;

FIG. 24 is a fragmentary perspective view of the vehicle seat of

FIG. 23 showing two work planes cut through the vehicle seat, and a sew line segment extending between the work planes;

DETAILED DESCRIPTION OF THE PREFERRED EMBODIMENTS

Figure 1:
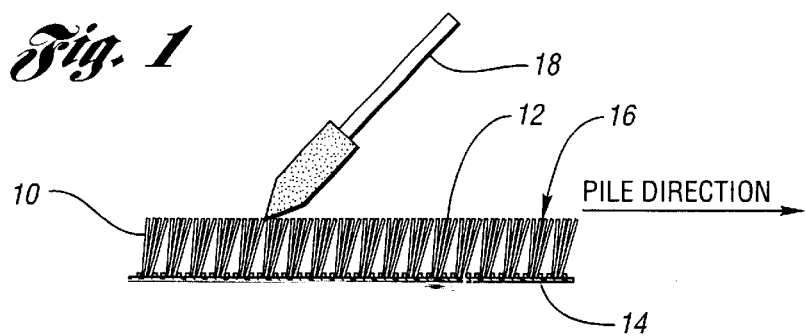
FIG. 1 is a side view of a specimen and brush for use with a marking resistance standard of the invention.

Typically, automobile manufacturers provide durability specifications for cover materials to be used as seat covers in vehicle seat applications. These specifications relate to such characteristics as material strength and wear resistance. These specifications, however, do not address material processability. As a result, cover materials initially selected for use in particular vehicle seat applications are, sometimes, later found to be undesirable from a processing standpoint. For example, it may be discovered that a previously selected cover material is unable to adequately conform to a desired vehicle seat contour without exhibiting excessive wrinkling. As another example, it may be discovered that a previously selected cover material tends to pucker at or near seam locations when used as a seat cover.

Realizing the need for practical material processability standards, the inventors of the present invention have developed a plurality of material processability standards for use in determining processability and, therefore, usability of a cover material as a seat cover in a particular vehicle seat application. The standards include standards for marking resistance, fabric pattern, pile bind, rippling resistance, laminate wrinkle resistance, raveling resistance, seam puckering, stretch, and elongation. One or more of these standards may be used to effectively screen multiple cover materials, so that a sufficiently processable cover material may be efficiently selected. Each of these standards is described below in detail.

First, however, several terms used throughout the application will be defined. These terms include machine direction, cross-machine direction, diagonal direction and pile. Machine direction is the direction in the plane of a cover material or specimen parallel to the direction of manufacture. Cross-machine direction is the direction in the plane of a cover material or specimen perpendicular to the direction of manufacture. Diagonal direction refers to a direction in the plane of a cover material or specimen extending at specified angles from the machine direction. For woven fabrics, the machine direction is known as warp direction and the cross-machine direction is known as fill direction. For knit fabrics, the machine direction is known as wale direction and the cross-machine direction is known as course direction. However, for knit fabrics, warp is frequently used in place of wale, and fill is used in place of course.

Pile refers to fibers or yarns that form the appearance surface or top surface of certain cover materials, such as woven pile fabric and knit pile fabric. Furthermore, woven pile fabric is frequently referred to as woven velour.

The standard for marking resistance provides a method for determining marking resistance of pile fabrics, napped fabrics and/or synthetic suedes that are used in seat covers of vehicle seats. Marking refers to the tendency of a cover material to acquire an imprint on a surface of the cover material when the cover material is pressed or disturbed. An example of marking is a palm print left on a fabric after a hand is pressed against the fabric. The method for determining marking resistance involves disturbing a surface of a particular cover material, as described below, and then comparing the surface with a reference chart, such as a gray scale chart including a plurality of reference pairs and having the characteristics shown below in Table 1.

TABLE 1

| Gray Scale Characteristics | | |
|---|---|---|
| Gray Scale Value | Color Difference, CIELAB ($\Delta E$) | Tolerance ($\pm$) |
| 5.0 | 0.0 | 0.2 |
| 4.5 | 0.8 | 0.2 |
| 4.0 | 1.7 | 0.3 |
| 3.5 | 2.5 | 0.3 |
| 3.0 | 3.4 | 0.4 |
| 2.5 | 4.8 | 0.5 |
| 2.0 | 6.8 | 0.6 |
| 1.5 | 9.6 | 0.7 |
| 1.0 | 13.6 | 1.0 |

Such a gray scale chart is available from American Association of Textile Chemists and Colorists (AATCC), and may be referred to as a gray scale for evaluating change in color.

Figure 2:
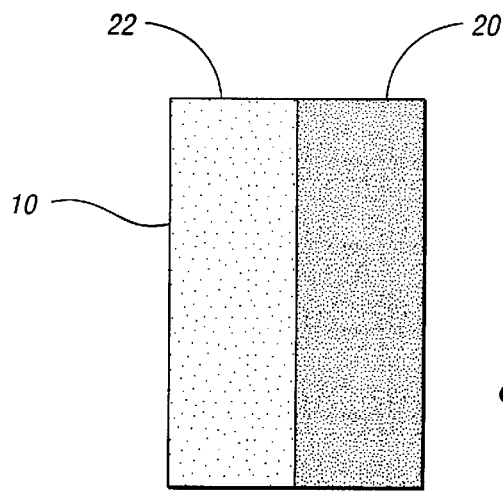
FIG. 2 is a top view of the specimen that has been brushed so as to form a light portion and a dark portion.
Figure 3:
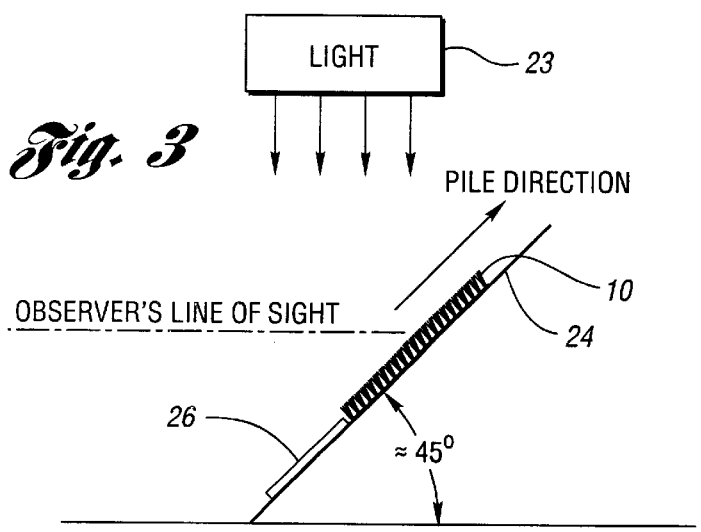
FIG. 3 is a side view of the specimen positioned beneath a light source for evaluation.

Referring to FIGS. 1 through 3, a detailed description of the method for determining marking resistance will now be provided. First, a specimen 10 of a cover material to be tested is cut into a suitable size, such as 102 millimeters (mm)×152 mm. The long dimension determines the direction of the specimen 10. Next, the specimen 10 is placed on a flat surface with pile 12 of the specimen 10 facing upwardly, and with the pile direction pointing away from the person conducting the test, who may be referred to as an observer. Pile direction is the direction the pile 12 tilts from ground or base 14 of the specimen 10 to pile surface 16. Pile direction is also referred to as nap direction. For cover materials that do not have obvious pile direction, two specimens of the cover material may be placed side by side with the machine direction aligned with the line of sight of the observer. One of the specimens may then be rotated 180°, and the specimen showing a lighter shade may be assumed to be the specimen having the pile direction pointing away from the observer.

Next, as shown in FIG. 1, the pile 12 is brushed with a suitable brushing member, such as a 51 mm wide foam brush 18, along a first direction, such as the pile direction. The downward force should be in the range of 100 to 150 grams. Pressing the foam brush 18 on a balance, prior to pressing the foam brush 18 on the specimen 10, may help in determining the downward force. A ruler or other suitable device may also be used to press down the bottom edge of the specimen 10 to inhibit the specimen 10 from sliding on the flat surface. Next, referring to FIG. 2, a first portion of the specimen 10, such as right half 20, is brushed one time against the pile direction so that the right half 20 may have a darker shade than a second portion, such as left half 22.

The specimen 10 is then placed in a light booth (not shown) beneath a light source 23 and on a flat surface 24 that is tilted at approximately 45° to the horizontal. The light booth is preferably a color matching light booth meeting the requirements of the American Society for Testing and Materials (ASTM) standard D 1729-96, Standard Practice for Visual Appraisal of Colors and Color Differences of Diffusely-illuminated Opaque Materials. The center of the specimen 10 should be at approximately the same level as the eyes of the observer. The right half 20 of the specimen 10 should be on the right hand side of the observer. Next, a gray scale chart 26, such as described above in detail, is placed immediately adjacent the bottom edge of the specimen 10 as shown in FIG. 3.

The observer then compares one or more of the reference pairs of the gray scale chart 26 to the right and left halves 20 and 22 of the specimen 10. Each reference pair provides a specific contrast level or color difference, and includes a specific gray scale value corresponding to the color difference. When comparing a particular reference pair to the specimen 10, the reference pair is preferably positioned immediately adjacent to the specimen 10. Furthermore, the observer should preferably have normal color vision and meet requirements specified in ASTM E 1499-97, Standard Guide for Selection, Evaluation and Training of Observers.

After the reference pair having a color difference most closely resembling the color difference of the right and left halves 20 and 22 has been selected, the appropriate gray scale value may then be recorded. In case the pile 12 is disturbed before a judgment can be made, the test should be started over.

The method may also include determining a marking resistance rating requirement for a particular vehicle seat, and comparing the gray scale value for the specimen 10 with the rating requirement. For example, the rating requirement for a particular vehicle seat may be set at a minimum of 2.5. In such a case, if the specimen 10 has a gray scale value below 2.5, then the cover material from which the specimen 10 was cut will not be considered suitable for use with the particular vehicle seat.

Additional details regarding evaluation of visual color difference with a gray scale may be found in ASTM D 2616-96, Standard Test Method for Evaluation of Visual Color Difference with a Gray Scale, and AATCC Evaluation Procedure 1, Gray Scale for Color Change.

The fabric pattern standard provides a method for evaluating processability of a cover material based on fabric pattern. The method involves visual appraisal of lines formed by characteristics, such as color, luster, texture, and/or pile height of yarns, of a particular cover material and determination of angles of such lines. Some lines in cover materials tend to accentuate misalignment that may occur in manufacturing of cover materials and/or in seat build processes. Contrast of detected lines is then determined. A gray scale chart, such as the gray scale chart described above with respect to the marking resistance standard, and a reference table, such as Table 2 shown below, may be used with this method to establish references for determining contrast of lines.

TABLE 2

Reference for the Contrast of Lines

| Gray scale value corresponding to the line and its surrounding | Contrast of line |
|---|---|
| 1–2 | High contrast |
| 2.5–3.5 | Medium contrast |
| 4–5 | Low contrast |

A high contrast line may be defined as a line in a fabric surface that is easy to detect or distinguish from its surroundings from any viewing direction and any viewing angle. In other words, a high contrast line has high contrast with its surroundings. A medium contrast line is a line in a fabric surface that is perceivable from most viewing directions and viewing angles. A low contrast line may be defined as a line in a fabric surface that is perceivable only when examined closely.

Figure 4:
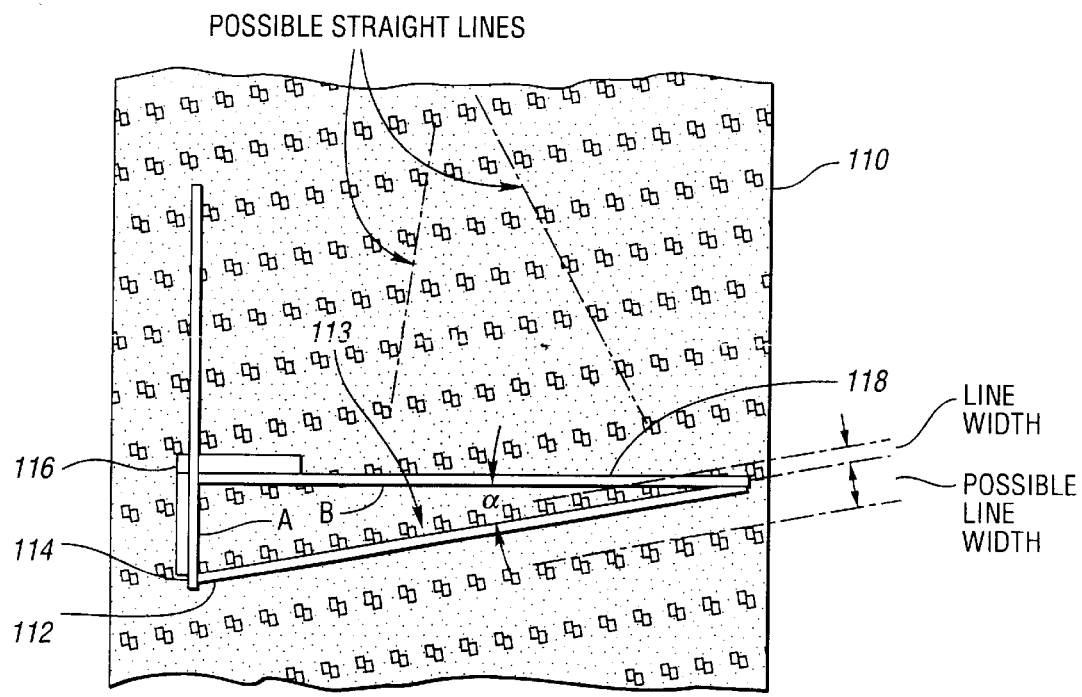
FIG. 4 is a top view of a specimen and apparatus for use with a fabric pattern standard of the invention.

Referring to FIG. 4, a detailed description of the method of the fabric pattern standard will now be provided. The method begins by obtaining a specimen 110 of a cover material to be tested. Preferably, an entire roll or bolt of a test sample of the cover material is used as the specimen 110, but not the first meter or so measured from either end. Alternatively, the specimen 110 may be a piece of the cover material that is as large as possible.

The specimen 110 should be laid down on a flat, horizontal surface. Next, the specimen 110 is viewed at a 0° viewing direction, which is preferably parallel to the machine direction and extends from the person conducting the test, or observer, toward the center of the specimen 110. The viewing distance between the eyes of the observer and the center of the specimen 110 is preferably maintained at approximately 500 mm, or other suitable distance. The viewing angle, which is the angle of the line of sight of the observer with respect to the plane of the specimen 110, may then be varied with respect to the flat surface so as to achieve the best perception of fabric patterns. A first straight edge 112 may then be placed on any generally straight line perceived on the specimen 110, such as line 113. When skewness and/or bow are present along a particular line, the first straight edge 112 should be placed so that the first straight edge 112 is a best fit to the skewed or bowed line.

Next, a second straight edge, such as a measuring ruler 114, is placed in the machine direction such that the measuring ruler 114 intersects the first straight edge 112. A square 116 may then be used to define a line that is perpendicular to the measuring ruler 114 and that extends from a portion of the measuring ruler 114 that is spaced away from the first straight edge 112. The square 116 is then used as a guide to place a third straight edge 118 along the cross-machine direction such that the third straight edge 118 intersects the measuring ruler 114 and the first straight edge 112 so as to form a right triangle. Preferably, the triangle should be as big as possible. Next, the lengths of the sides of the triangle that are perpendicular to each other are measured. The side parallel to the machine direction may be labeled as A, and the side parallel to the cross-machine direction may be labeled as B, as shown in FIG. 4. The line angle α formed by side B and the line 113, which is the hypotenuse of the triangle, may be calculated using the following equations:

$$\alpha = \text{ARCTAN}(A_i/B_i) \times 180/\pi, \text{ if ARCTAN returns in radians, or}$$

$$\alpha = \text{ARCTAN}(A_i/B_i), \text{ if ARCTAN returns in degrees,}$$

where i=1, 2, 3, etc. depending on the number of generally straight lines observed in any given viewing direction. Generally, line angle refers to the angle of a line with respect to the cross-machine direction of the specimen 110.

If the line angle is less than or equal to a first line angle limit, such as 15°, or greater than or equal to a second line angle limit, such as 75°, the width of the line 113 is then measured to the nearest mm. The contrast level of the line 113 with respect to an adjacent portion of the specimen is then determined in any suitable manner. For example, the contrast level of the line 113 may be determined by using the gray scale chart described above, along with Table 2. The above process is then repeated for each generally straight line perceived in the specified viewing direction. The line angle, width and contrast level of each perceived line are then recorded. Lines that have been measured may also be appropriately marked to avoid redundant measurement.

The viewing direction or the specimen 110 is then rotated 90° counterclockwise. Next, the above steps are repeated until the viewing direction returns to 0°. Only new generally straight lines that have not been detected previously need to be measured and/or otherwise evaluated. Furthermore, if a particular line does not extend at least a predetermined distance, such as 150 mm, the line may be disregarded.

All detected lines are then rated in any suitable manner, such as by using Table 3 shown below.

TABLE 3

Rating of Fabric Pattern

| Lines within 15° of machine or cross-machine direction | Rating |
|---|---|
| None | 5 |
| line width ≦ 2 mm, and low contrast | 4 |
| line width ≦ 5 mm, and low contrast | 3 |
| line width ≦ 10 mm, and low contrast; or, line width ≦ 2 mm, and medium contrast | 2 |
| line width > 10 mm, and low contrast; or, line width > 2 mm, and medium contrast; or any high contrast line | 1 |

The lowest rating may then be used to determine the rating of the entire specimen 110. Because the rating of the lines includes subjectivity, all interested parties should reach a mutually agreed upon rating in cases where the rating is in doubt. Typically, lines having angles greater than 15° and less than 75° do not tend to accentuate misalignment that may occur in manufacturing of cover materials and/or in seat build processes. As a result, such lines may be disregarded during the rating process.

The method may also include determining a fabric pattern rating requirement for a particular vehicle seat, and comparing the rating for the entire specimen 110 with the rating requirement. For example, the rating requirement for a particular vehicle seat may be set at a minimum of 3. In such a case, if the specimen 110 has a rating below 3, then the cover material associated with the specimen 110 will not be considered suitable for use with the particular vehicle seat.

The pile bind standard provides a method for determining pile bind for a woven pile cover material. Pile bind is a measure of how well the pile of a particular cover material is bound to a base such as ground yarns.

Figure 5:
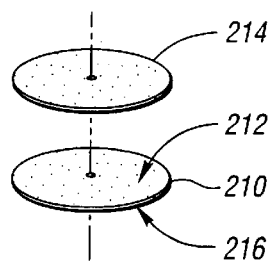
FIG. 5 is a perspective view of a specimen and mounting card for use with the pile bind standard of the invention.
Figure 6:
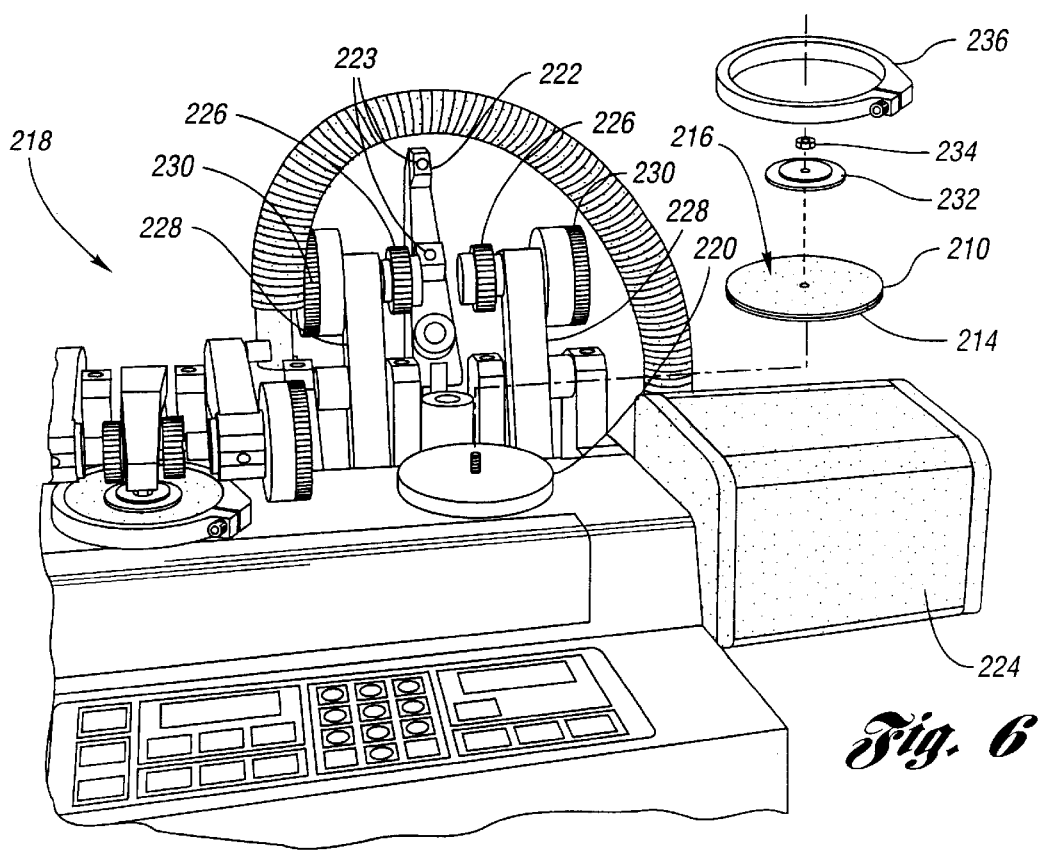
FIG. 6 is a perspective view of the specimen and an apparatus for testing the specimen according to the pile bind standard.
Figure 7:
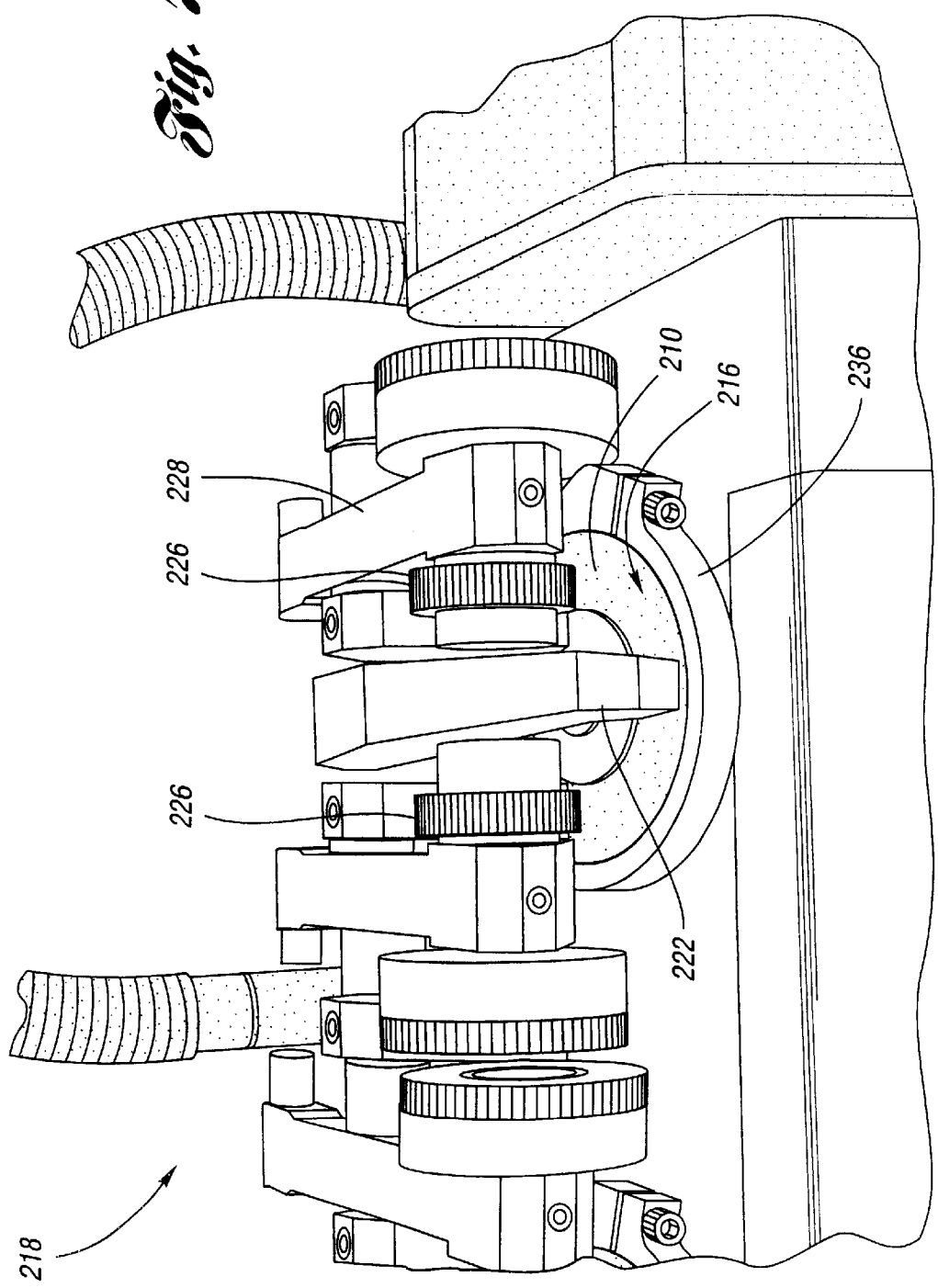
FIG. 7 is a perspective view of the specimen and apparatus of FIG. 5, with the specimen loaded onto the apparatus.

Referring to FIGS. 5–7, a detailed description of the method of the pile bind standard will now be provided. First, a specimen 210 of a cover material to be tested is cut to any suitable size, such as 152 mm×152 mm. The specimen 210 is then laid on a flat surface with pile surface 212 facing upwardly. Referring to FIG. 5, a suitable mounting card 214, such as an S-36 mounting card or equivalent, is then mounted to the pile surface 212 of the specimen 210. Excess portions of the specimen 210 may then be removed, such as by cutting the specimen 210, so as to conform the specimen 210 to the shape of the mounting card 214. A hole, such as a 6 mm hole, may then be punched through the center of the specimen 210. The specimen 210 should be checked for any wrinkles or uneven surfaces. Backside or back surface 216 of the specimen 210 should be free of wrinkles. If wrinkles are detected on the back surface 216, the specimen 210 should be discarded.

Referring to FIGS. 6 and 7, the specimen 210 may then be tested using any suitable apparatus, such as a rotary platform, double-head abraser 218 available from Taber Industries of N. Tonawanda, N.Y. The abraser 218 preferably meets the requirements specified in ASTM D 3884-92, Standard Test Method for Abrasion Resistance of Textile Fabric. Furthermore, the abraser 218 is preferably prepared and calibrated as specified in ASTM D 3884-92.

The abraser 218 includes a rotatable platform 220, an adjustable vacuum or suction nozzle 222 having two suction openings 223, a vacuum source 224 connected to the suction nozzle 222, and two abrasive members such as abrasive wheels 226 supported by adjustable wheel support arms 228. While any suitable abrasive wheels may be used, the abrasive wheels 226 are preferably CS-10 abrasive wheels, with each wheel having a diameter of 45 mm or greater. The two abrasive wheels 226 should be in similar condition, and new wheels should be avoided if possible. Wheels that have worked more than 1000 cycles are not considered new wheels. Furthermore, each revolution of the platform 220 represents one cycle.

Before the specimen 210 is tested on the abraser 218, the abrasive wheels 226 are preferably resurfaced in any suitable manner. For example, a resurfacing disk (not shown), such as an S-11 resurfacing disk or equivalent, may be mounted on the platform 220. The suction nozzle 222 is then positioned approximately 2 mm above the resurfacing disc, and the abrasive wheels 226 are moved into engagement with the resurfacing disk. Next, the vacuum source 224 is activated, such as by selecting a vacuum setting of 70. The abrasive wheels 226 are then resurfaced for approximately 10 cycles under a 1000 gram load. Load may be applied to the abrasive wheels 226, for example, by attaching weights 230 to the wheel support arms 228.

If the abrasive wheels 226 are new, the abrasive wheels 226 may first be resurfaced against the resurfacing disc for 10 cycles under a 1000 gram load. The abrasive wheels 226 may then be used for another 1000 cycles against a separate break-in specimen (not shown). The break-in specimen may be prepared in a similar manner as described above with respect to the specimen 210, except that the non-pile side or back surface of the break-in specimen is bonded to a mounting card. Furthermore, the abrasive wheels 226 are preferably engaged with the pile surface of the break-in specimen. Next, the abrasive wheels 226 may be resurfaced again for another 10 cycles using the resurfacing disk. After the abrasive wheels 226 have been sufficiently resurfaced, the resurfacing disk is removed and the abraser 218 is cleaned of lint and abrasive particles.

Next, the specimen 210 may be loaded onto the platform 220 with the back surface 216 facing upwardly. The specimen 210 is then secured to the platform 220 in any suitable manner. For example, a clamp plate or retainer plate 232 and nut 234 may be placed over the specimen 210 to hold the specimen 210 in place. A clamp ring 236 is also used to further secure the specimen 210 to the platform 220. Referring to FIG. 7, the suction nozzle 222 is then positioned approximately 2 mm above the specimen 210, and the wheel support arms 228 are lowered so as to engage the abrasive wheels 226 with the back surface 216 of the specimen 210.

The specimen 210 may then be run for a predetermined number of cycles, such as 50, at a predetermined load, such as 1000 grams, and a predetermined vacuum setting, such as 70. The specimen 210 is then unloaded from the abraser 218 and is cleaned, such as with a vacuum. The mounting card 214 is then removed from the specimen 210, and the specimen 210 is held against a light source (not shown), such as a ceiling light or desk light, with the pile surface 212 facing the light source. The back surface 216 of the specimen 210 is then examined for holes where pile tufts have been lost. Each lost pile tuft typically causes two holes. The number of holes are then counted. If the number of holes exceeds a predetermined number, such as 50, counting may be discontinued. Pile loss may then be determined using the following equations:

pile loss=number of holes/2, if the number of holes is 50 or less, or pile loss>25, if the number of holes is more than 50.

The method may also include determining a pile bind requirement for a particular vehicle seat, and comparing the pile loss of the specimen 210 to the pile bind requirement. For example, pile bind requirement for a particular vehicle seat may be set at 0. In such a case, if the specimen 210 has any pile loss, then the cover material from which the specimen 210 was cut will not be considered suitable for use with the particular vehicle seat.

The rippling resistance standard provides a method for determining rippling resistance of cover materials to be used as seat covers. Rippling refers to the tendency of a cover material to form wrinkles when the cover material is stretched. The direction of each wrinkle is typically parallel to the loading or stretch direction.

Figure 8:
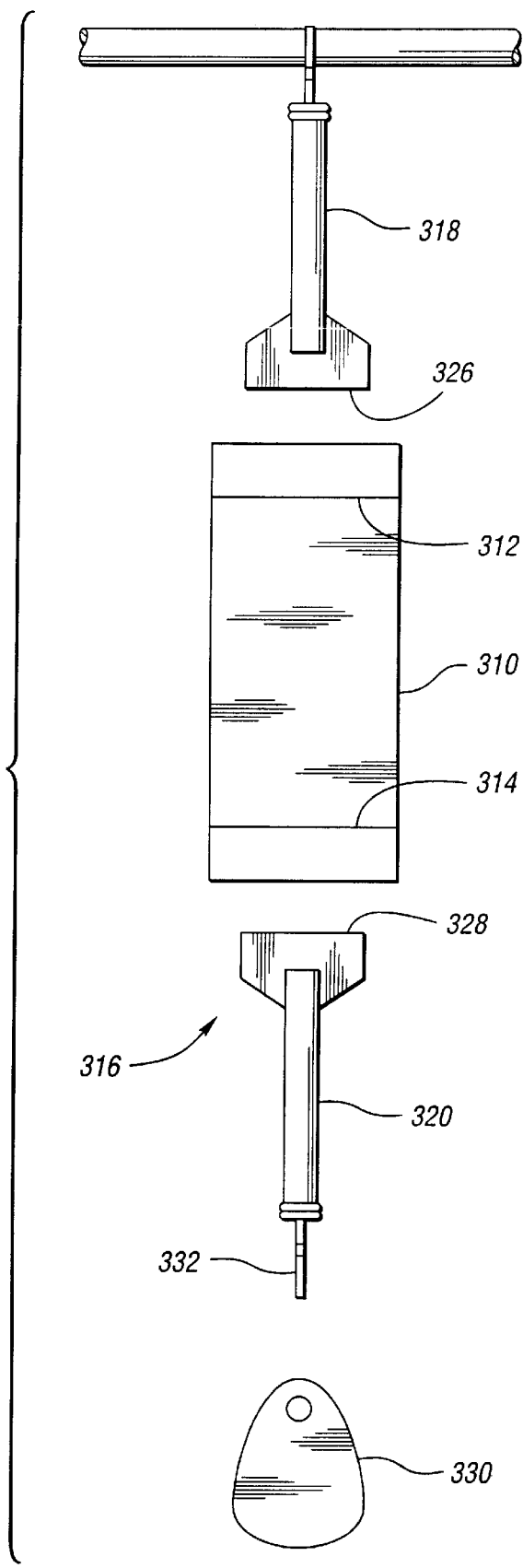
FIG. 8 is an exploded view of a specimen and clamping system for use with a rippling resistance standard of the invention.
Figure 9:
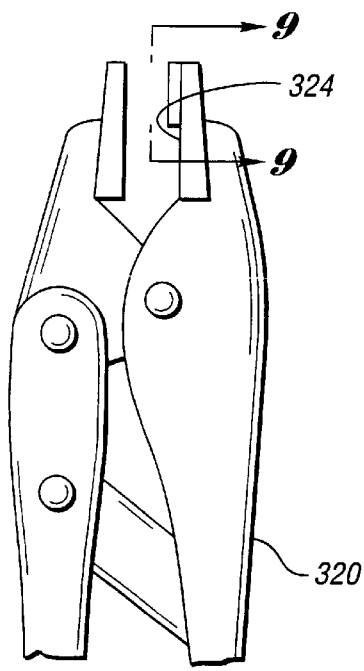
FIG. 9 is a fragmentary side view of a lower clamp of the clamping system of FIG. 8.
Figure 10:
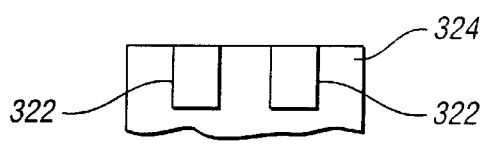
FIG. 10 is a fragmentary view of the lower clamp viewed in the direction of the arrows shown in FIG. 9.

Referring to FIGS. 8 through 10, a detailed description of this method will now be provided. First, a test specimen 310 of a cover material to be tested may be cut to any suitable size, such as 102 mm×267 mm. The long dimension determines the direction of the specimen 310. A first line 312 is then drawn on the non-pile side of the specimen 310 approximately 38 mm, or other suitable distance, away from one of the short edges and perpendicular to the direction of the specimen. A second line 314 is then drawn 203 mm, or other suitable distance, away from the first line 312 and perpendicular to the direction of the specimen. The lines 312 and 314 can be drawn before cutting the specimen 310. The specimen is then loaded into a clamping system 316 having first and second or top and bottom clamps 318 and 320, respectively. The clamps 318 and 320 may be similar to the clamps identified in Society of Automotive Engineers (SAE) Standard J855, Test Method of Stretch and Set of Textiles and Plastics, except that the bottom clamp 320 is modified as described below in detail. Instead of having one grip face as required in SAE J855, the bottom clamp 320 has two spaced grip points 322 as shown in FIG. 10. These grip points 322 may be formed in any suitable manner such as by attaching spacers to a face 324 of bottom clamp 320.

Next, the first line 312 is aligned with bottom edge 326 of the top clamp 318, and then the top clamp 318 is closed. The first line 312 should be facing the person conducting the test. The second line 314 is then aligned with top edge 328 of the bottom clamp 320, and then the bottom clamp 320 is closed. Suitable weight 330 may then be added to hook end 332 of the bottom clamp 320 so as to apply a tensile force to the specimen 310. While any suitable amount of weight may be used, the combined weight of the added weight 330 and the bottom clamp 320 is preferably 2268 grams.

Figure 11:
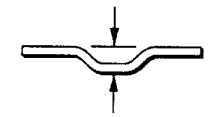
FIG. 11 is a fragmentary, horizontal cross-sectional view of the specimen of FIG. 8, showing a ripple formed in the specimen.

Next, both sides of specimen 310 are examined for wrinkles. The depth of the deepest wrinkle is then measured. For example, a first ruler may be used to form a line along peaks of the deepest wrinkle, and a second ruler may be used to measure the depth of the deepest wrinkle to the nearest mm. As shown in FIG. 11, the depth of a wrinkle may be determined by measuring the lateral dimension from adjacent peaks to a valley of the wrinkle. The specimen 310 may then be rated in any suitable manner, such as by using Table 4 shown below.

TABLE 4

Rating of Rippling Resistance

| Observation | Rating |
| --- | --- |
| No wrinkle | 5 |
| Wrinkle depth: $\leq 1$ mm | 4 |
| 1 mm < Wrinkle depth $\leq$ 3 mm | 3 |
| 3 mm < Wrinkle depth $\leq$ 5 mm | 2 |
| 5 mm < Wrinkle depth | 1 |

The method may also include determining a rippling resistance rating requirement for a particular vehicle seat, and comparing the rating of the specimen 310 to the rippling resistance rating requirement. For example, rippling resistance rating requirement for a particular vehicle seat may be set at a minimum of 3. In such a case, if the specimen 310 has a rating below 3, then the cover material from which the specimen 310 was cut will not be considered suitable for use with the particular vehicle seat.

The laminate wrinkle resistance standard provides a method for determining wrinkle resistance of laminates used as seat covers for vehicle seats. More specifically, the laminate wrinkle resistance standard provides a method for determining wrinkle resistance of laminates when the laminates are bent. The laminate wrinkle resistance standard may also include a method for determining laminate curl, as explained below in detail.

The term laminate is used to describe a cover material that includes a cover layer, such as fabric or vinyl, bonded to a slab foam or foam sheet. The term bi-laminate is used to describe a laminate formed with a cover layer and a foam sheet. The term tri-laminate is used to describe a laminate formed with a cover layer bonded to one side of a foam sheet, and a scrim bonded to the other side of the foam sheet.

Figure 12:
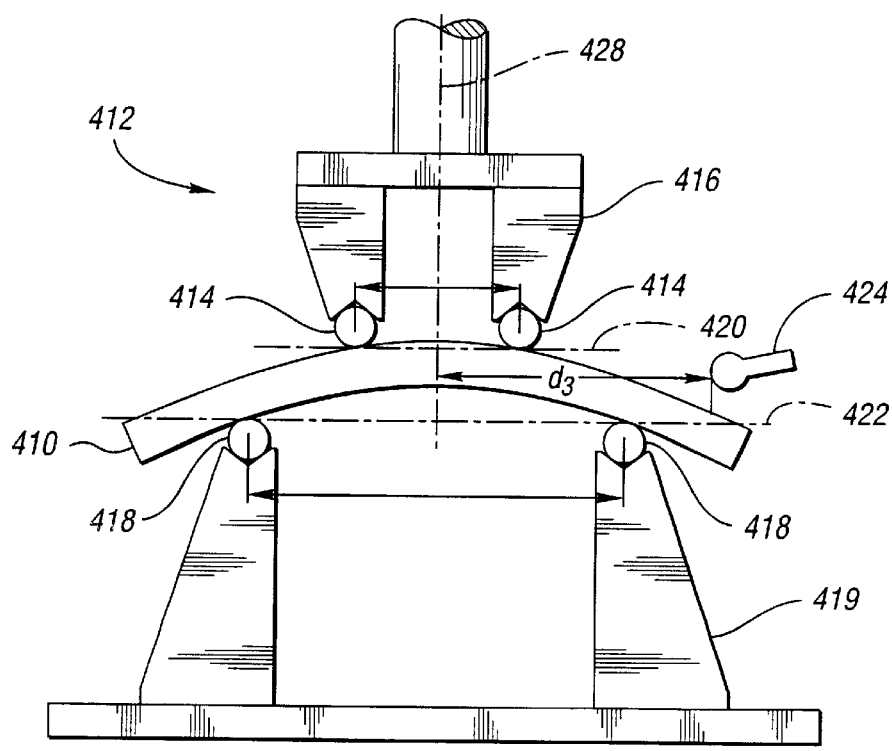
FIG. 12 is a schematic view of a specimen and apparatus for testing the specimen in accordance with a laminate wrinkle resistance standard of the invention.

Referring to FIG. 12, the method for determining laminate wrinkle resistance will now be described. First, a specimen 410 of a cover material to be tested is cut into any suitable size, such as 152 mm by 203 mm. Preferably, but not necessarily, the specimen 410 is taken from the third layer from the center of a roll of cover material. The long dimension of the specimen 410 determines the direction of the specimen 410.

Figure 13:
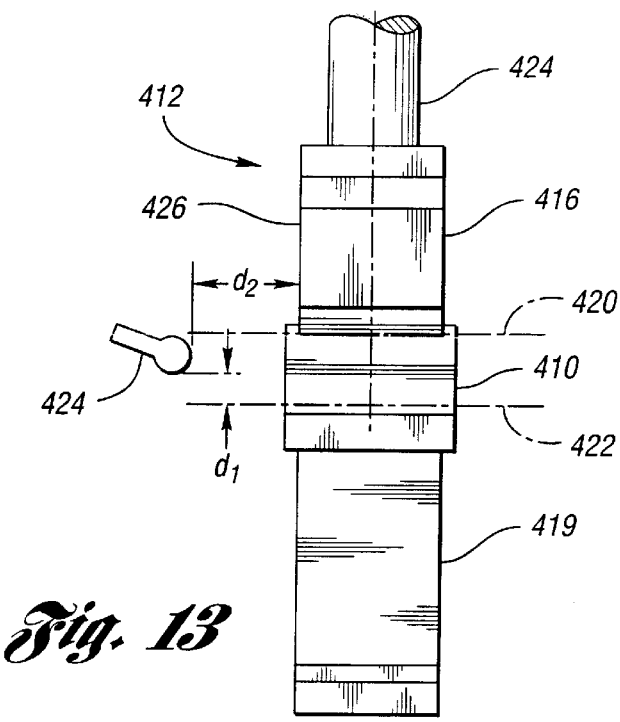
FIG. 13 is a side view of the apparatus shown in FIG. 12.

Any suitable bending apparatus may then be used to test the specimen 410. For example, FIGS. 12 and 13 show a bending apparatus 412 that is similar to a four-point flexural fixture, available from Instron Corporation of Canton, Mass. The bending apparatus 412 has two loading elements such as load noses 414 supported by an electronically controlled, movable upper support member 416, and two support elements such as support noses 418 supported by lower support member 419. The distance between the load noses 414, from load nose axis to load nose axis, is referred to as load span, and the distance between the support noses 418, from support nose axis to support nose axis, is referred to as support span. While the spans may be set to any suitable dimension, in one embodiment of the invention the load span is set to 38.1 mm, and the support span is set to 114.3 mm.

The speed of the support member 416 may be set to any suitable speed, such as 102 mm per minute. The load noses 414, which define a load plane 420, are then adjusted so that the load plane 420 is positioned at a predetermined distance, such as 50 mm, above a support plane 422 defined by the support noses 418. The position of the support member 416, which may be referred to as an initial or first position of the support member 416, is then marked as zero.

The thickness of the specimen 410 is then measured, such as according to ASTM D1777-96, Standard Test Method for Thickness of Textile Materials, or equivalent standard. This thickness is preferably measured to the nearest 0.1 mm, and is recorded as L1. A flashlight 424 or other source of light is then set at a first distance $d_1$ above the support plane 422, at a second distance $d_2$ in front of a front face 426 of the bending apparatus 412, and at a third distance $d_3$ to the side of the center line of the bending apparatus 412. The distances $d_1$, $d_2$ and $d_3$ may be any suitable distances, such as approximately 25 mm, approximately 100 mm and approximately 100 mm, respectively. The flashlight 424 should be pointed at an axis 428 of the bending apparatus 412 at the level of the support plane 422. The flashlight 424 illuminates the specimen 410 to aid in the detection of wrinkles during the test.

The specimen 410 is then loaded on the bending apparatus 412 and is centered with respect to the load noses 414 and the support noses 418. The load applied to the support member 416 is then zeroed, and the support member 416 is moved downwardly until the load noses 414 touch the specimen 410. The displacement of the support member 416 from the zero position to this position is then measured to the nearest 0.1 mm, and is recorded as L2. The bending apparatus 412 is then activated so as to move support member 416 downwardly and apply load to the specimen 410, thereby causing the specimen 410 to bend. When and if wrinkles show on the specimen 410, the displacement of the support member 416 is marked and/or the bending apparatus 412 is stopped immediately. Such wrinkles may show outside the load noses 414, between the load noses 414, and/or under the load noses 414. The displacement of the support member 416 from the zero position to this point is measured to the nearest 0.1 mm, and is recorded as L3. If no wrinkle occurs when the support member 416 reaches a predetermined displacement, such as 80 mm, then the test is discontinued. In such a case, L3 is recorded as 80 mm.

The wrinkle resistance index (WRI) may then be determined using the following equation:

$$WRI=0.16\times(L1+L3)+0.01\times(L1+L3)^2,$$

where L1 is the thickness of the specimen 410 in mm, and L3 is the displacement of support member 416 when a wrinkle first appears.

Laminate curl (CURL), measured in mm, may also be determined using the following equations:

$$CURL=50.0-L2-L1, \text{ if } (L2+L1)<50 \text{ mm}$$

$$CURL=0, \text{ if } (L2+L1)>50 \text{ mm},$$

where L2 is the displacement of support member 416 in mm when the load noses 414 touch the specimen 410. If the above process is performed multiple times for the same cover material, the average WRI and average CURL may then be determined and recorded. Furthermore, the above process may be performed in various directions with other specimens.

The method may also include determining a wrinkle resistance requirement and a laminate curl requirement for a particular vehicle seat, and comparing the WRI and CURL, or average WRI and average CURL, of the specimen 410 to the wrinkle resistance requirement and the laminate curl requirement, respectively. For example, the wrinkle resistance requirement may be set at a minimum of 50, and the laminate curl requirement may be set at a maximum of 25 mm for a particular vehicle seat. In such a case, if the specimen 410 has a WRI less than 50, or a CURL greater than 25 mm, then the cover material from which the specimen 410 was cut will not be considered suitable for use with the particular vehicle seat.

The raveling resistance standard provides a method for determining raveling resistance of cover materials that include woven fabrics and are intended for use as seat covers. Raveling of a cover material may be defined as the tendency of yarns to unweave or fall out of the cover material near cut edges of the cover material.

Figure 14:
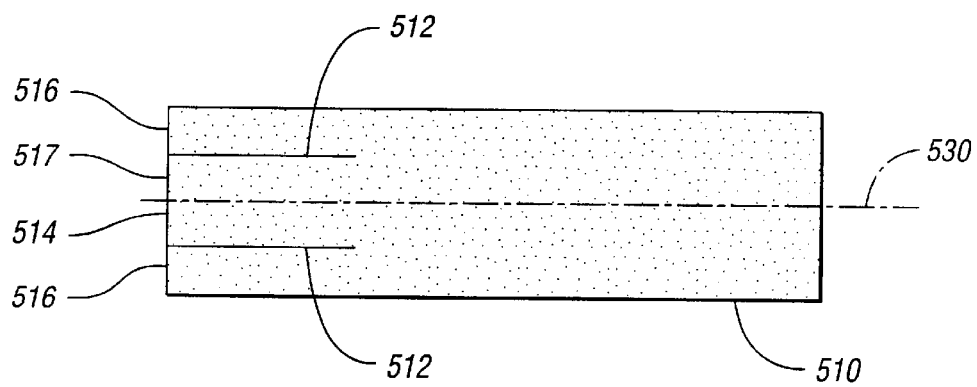
FIG. 14 is a top view of a specimen for use with a raveling resistance standard of the invention.
Figure 15:
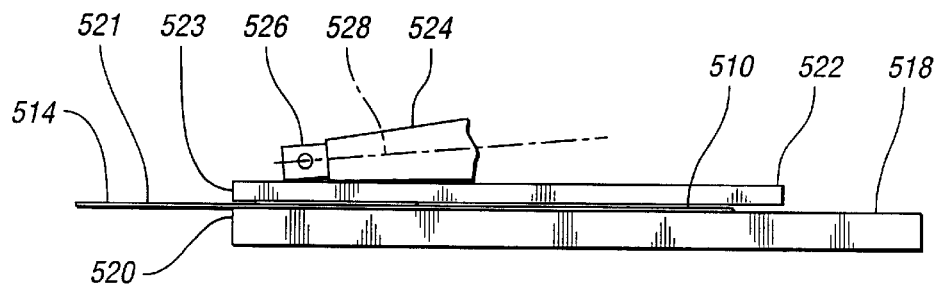
FIG. 15 is a side view of the specimen of FIG. 14 and an arrangement for testing the specimen in accordance with the raveling resistance standard.
Figure 16:
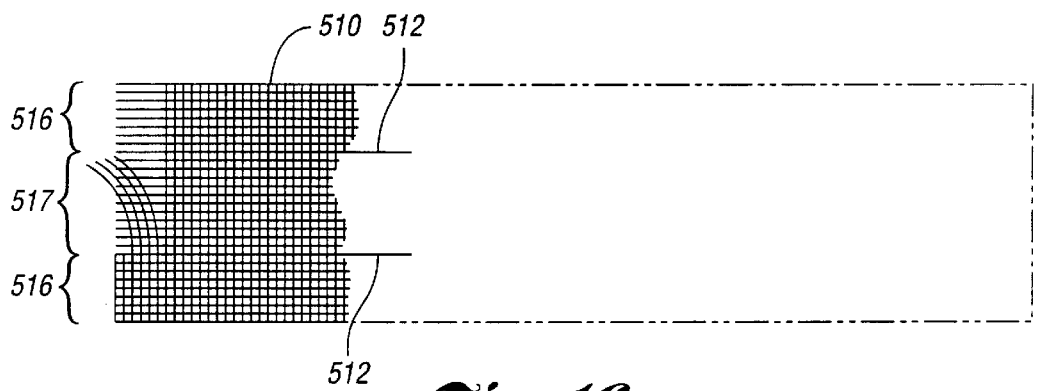
FIG. 16 is a top view of the specimen of FIGS. 14 and 15 after testing has been conducted.

Referring to FIGS. 14 through 16, the method for determining raveling resistance will now be described. First, a specimen 510 of a cover material to be tested may be cut into any suitable size, such as 50 mm by 180 mm. The short dimension of the specimen 510 determines the direction of the specimen 510. Next, two spaced lines 512, extending approximately 50 mm in a direction perpendicular to the direction of the specimen 510, are drawn on the specimen 510 starting at short end 514. Approximately five yarns extending in the direction of the specimen 510 are then removed from the short end 514, thereby creating an exposed portion (not shown) of the specimen 510. The yarns may be removed in any suitable manner, such as by using a pick or a needle.

Next, the exposed portion of the specimen 510 is cut off, such as by using scissors, so as to trim the short end 514. The trimmed short end 514 should be parallel to the direction of the specimen 510. Next, the specimen 510 is cut along the lines 512 so as to form two flap portions or flaps 516 and a middle portion or section 517. If the specimen 510 is from a laminate cover material having a foam sheet thickness greater than 1 mm, the foam sheet thickness should be reduced to approximately 1 mm between the lines 512. Unevenness in the foam sheet thickness is permitted as long as the thickness is less than 1 mm.

Next, with the appearance surface of the specimen 510 facing upwardly, the two flaps 516 are folded 180° and are secured with tape if necessary. The specimen 510 is then placed on a flat surface 518 with the short end 514 flush with an edge 520 of the flat surface 518. The specimen 510 is then pushed over the edge 520 of the flat surface 518 until a portion 521 of the specimen 510 overhangs the edge 520 approximately 40 mm, as shown in FIG. 15. A ruler placed against the edge 520 of the flat surface 518 and held horizontally can be used to support the overhanging portion 521 of the specimen 510 and to measure the overhanging length. The short end 514 of the specimen 510 should also be parallel to the edge 520 of the flat surface 518.

A suitable plate, such as a stainless steel plate 522 measuring 100 mm by 150 mm and having a thickness in the range of 0.5 mm to 2 mm, is then placed on top of the specimen 510. Short edge 523 of the steel plate 522 should be flush with the edge 520 of the flat surface 518. A blow gun 524, such as a standard safety compressed air blow gun with a maximum outlet pressure of 207 kilopascals (KPa), is then placed on the steel plate 522 with a head 526 of the blow gun 524 positioned approximately 10 mm behind the short edge 523 of the steel plate 522. Axis 528 of blow gun 524 should line up with axis 530 of the specimen 510. Furthermore, axis 528 of the blow gun 524 should form an angle of approximately 5° with respect to the steel plate 522. Small blocks or spacers can be attached to the steel plate 522 to facilitate positioning of the blow gun 524.

The blow gun 524 is then connected to a source of compressed air (not shown) capable of producing sufficient line pressure, such as a line pressure of approximately 689

KPa. An air pressure regulator (not shown) may also be connected between the source of compressed air and the blow gun 524 if necessary to reduce line pressure to 689 KPa. Air flow through the blow gun 524 is preferably, but not necessarily, approximately 566 liters per minute at 689 KPa.

If specimen 510 is un-laminated, air is then blown through the blow gun 524 at full volume for a sufficient amount of time, such as approximately 15±1 seconds. If specimen 510 is laminated, air is blown at full volume for approximately 30+1 seconds. While air is being blown onto the specimen 510, the overhanging portion 521 of the specimen 510 should flap up and down rapidly and make a flapping noise. If the overhanging portion 521 does not flap or does not make the flapping noise, the specimen 510 and blow gun 524 should be checked. The blow gun 524 and steel plate 522 are then removed, and the flaps 516 of the specimen 510 are unfolded.

The middle section 517 of the specimen 510 may have more short yarns raveled along one cut line 512 than the other cut line 512, as shown in FIG. 16. Yarns that raveled along one of the cut lines 512 but not along the other cut line 512 may be counted as raveled yarns. The specimen 510 is then examined to determine the cut line 512 along which more yarns have raveled. Short yarns from the flap 516 that is adjacent to this cut line 512 are then removed until the short yarns are aligned with the first non-raveled yarn in the middle section 517 of the specimen 510. The number of yarns removed is then recorded. In the case that yarns are dislodged but not raveled, the number of yarns dislodged may also be counted as raveled yarns. The specimen 510 may then be rated in any suitable manner, such as by using Table 5 shown below.

TABLE 5

Rating of Specimens

| Number of yarns raveled or dislodged | Rating |
| --- | --- |
| None | 5 |
| 1 or less | 4 |
| 2 or less | 3 |
| 3 or less | 2 |
| more than 3 | 1 |

The method may also include determining a raveling resistance requirement for a particular vehicle seat, and comparing the rating of the specimen 510 to the raveling resistance requirement. For example, the raveling resistance requirement for a particular vehicle seat may be set at a minimum of 3. In such a case, if the specimen 510 has a rating below 3, then the cover material from which the specimen 510 was cut will not be considered suitable for use with the particular vehicle seat.

Figure 17:
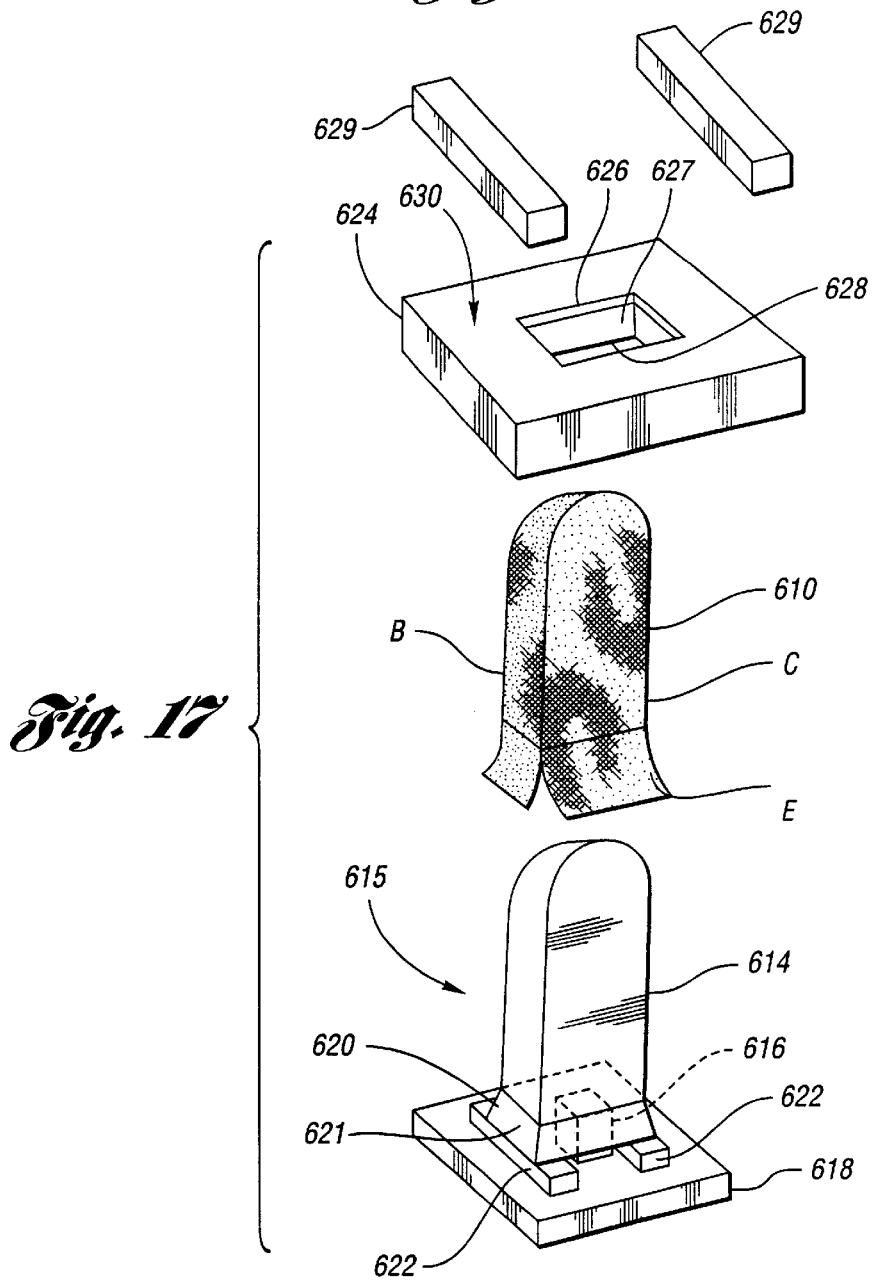
FIG. 17 is an exploded perspective view of an apparatus for testing a cover in accordance with a seam puckering standard of the invention.
Figure 22B:
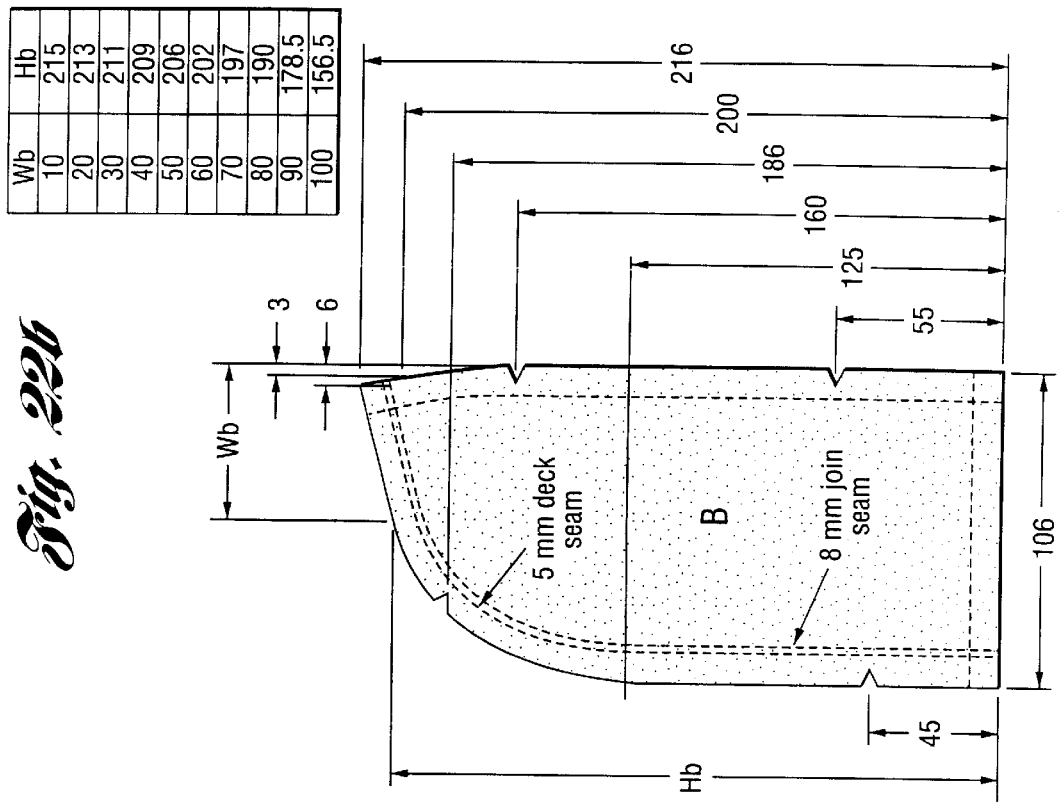
FIG. 22 (22a–22e) is an enlarged view of the panels of FIG. 18.
Figure 22A:
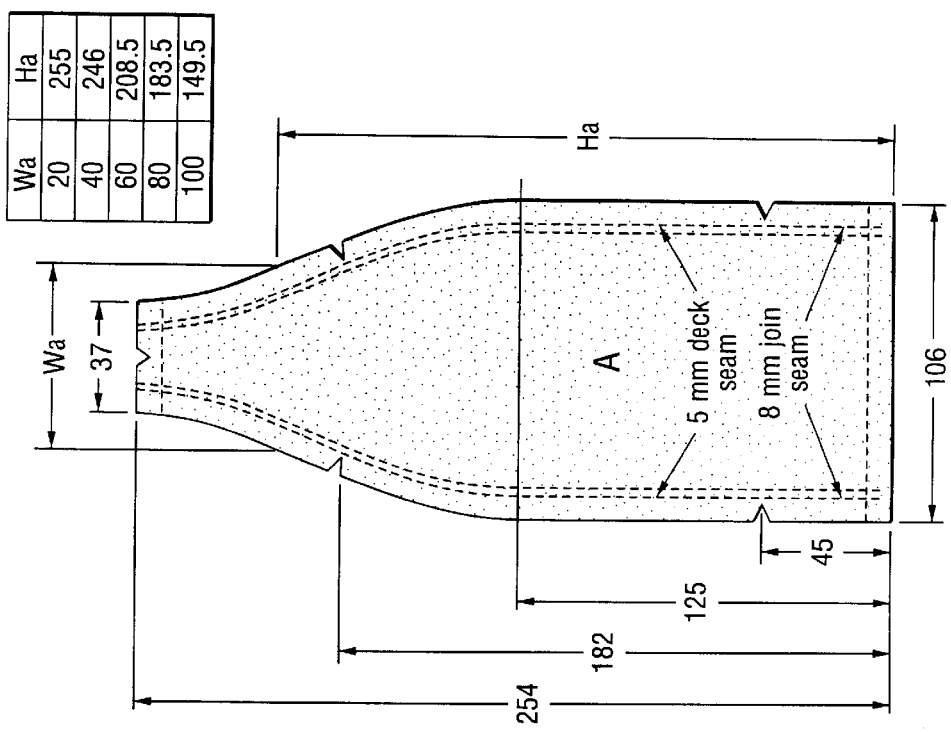
Figure 22C:
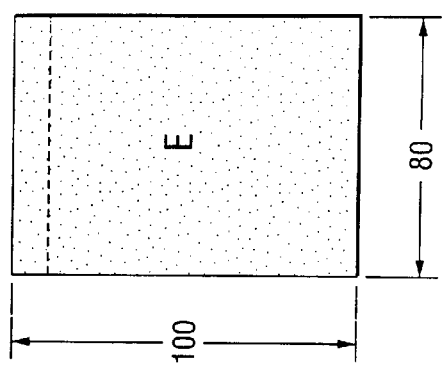
Figure 22B:
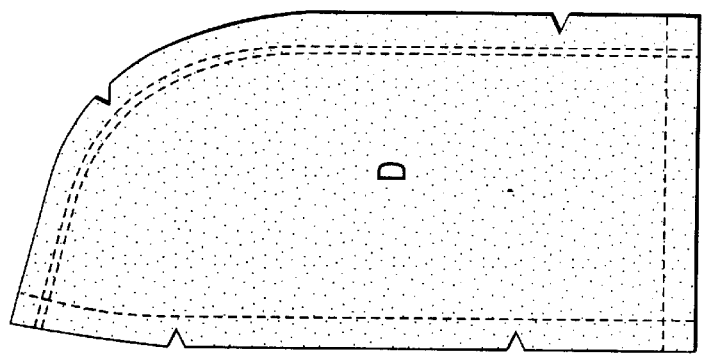
Figure 22A:
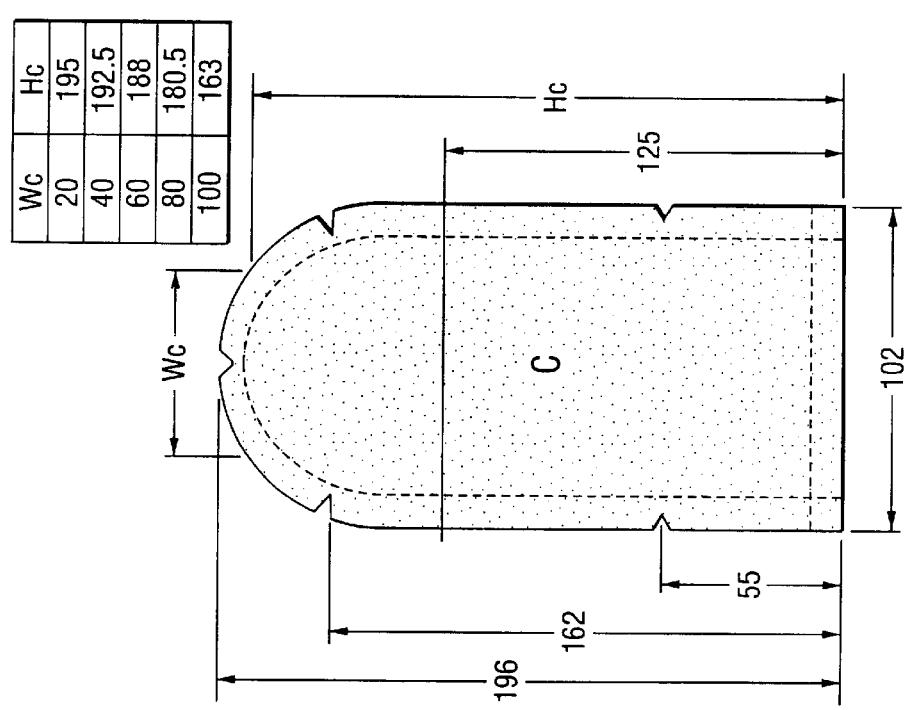

The seam puckering standard provides a method for evaluating seam puckering, which is the tendency of a cover material to form seam puckers. A seam pucker refers to one or more small wrinkles that radiate or otherwise extend from a seam or sew line. Referring to FIG. 17, the method generally involves forming a cover material into a generic cover, such as specimen or cover 610, which is positioned on a generic form, such as form 614. The form 614 preferably represents contours in seats, including headrests and armrests, that tend to show puckers along seams. Weights are then applied to the cover 610 to keep it under tension. The cover 610 is then examined for seam puckers.

A more detailed description of the method will now be provided. Referring to FIGS. 17 and 18, panels A, B, C, D, and E are cut from a cover material to be tested. The panels A–E are then sewn together, preferably using a sewing machine and thread that represent the needle and thread used in seat cover production, so as to form cover 610. For example, number 92 thread may be used for top and bottom threads, and a number 140 ballpoint needle may be used with the sewing machine. The panels A–E may be joined in any suitable order to form the cover 610. For example, panels B and D may be joined first to panel A. Panels B and D may then be joined to panel C. Alignment features of the panels A–D, such as notches 612, may be used to properly align the panels A–D when the panels A–D are joined together. A separate panel E may then be joined to each of the panels A–D. After sewing has been completed, the cover 610 is inverted so that the appearance surface of the cover material is exposed.

Referring to FIG. 17, the cover 610 is then positioned on form 614 of test apparatus 615, while making sure sew lines or seams of the cover 610 are not skewed or twisted. The form 614 has a projection 616 that is supported by a base 618. Furthermore, an inner wedge ring 620, having tapered side walls 621, is positioned around the projection 616 and is supported by spacers 622.

The dimensions and configuration of the form 614 are preferably selected so that the form 614 represents contours in a typical seat that tend to show puckers along seams. While the form 614 may have any suitable configuration, FIGS. 19 through 21 show preferred dimensions, in millimeters, and configuration of the form 614. Furthermore, the form 614 may comprise any suitable material such as wood, metal and/or plastic.

The dimensions of the panels A–E are preferably selected so that the cover 610 fits closely around the form 614. While the panels A–E may have any suitable configuration, FIG. 22 shows preferred dimensions, in millimeters, of the panels A–E. Because panel D is symmetrical to panel B, see panel B for dimensions of panel D.

Returning to FIG. 17, the cover 610 may then be adjusted if necessary to achieve a proper fit between the cover 610 and the form 614. Next, an outer wedge ring 624, having a first opening 626, tapered side walls 627 and a second opening 628 that is larger than the first opening 626, is positioned over the cover 610 with the second opening 628 facing downwardly. The outer wedge ring 624 is then positioned proximate the inner wedge ring 620 so that panels E of the cover 610 are sandwiched between the tapered side walls 621 and 627 of the inner and outer wedge rings 620 and 624, respectively. The outer wedge ring 624 may be tapped lightly so that the two rings 620 and 624 hold the cover 610 securely in place. While the tapered side walls 621 and 627 may have any suitable taper, each tapered side wall 621 and 627 preferably defines a 10° angle with a vertical line.

Next, the spacers 622 are removed from beneath the inner wedge ring 620 so that the inner wedge ring 620 may move along the projection 616. One or more weights 629 may then be loaded on a top surface 630 of the outer wedge ring 624. The weights 629 should be symmetrical to an axis of wedge rings 620 and 624. While any suitable load may be applied to the cover 610, in one embodiment of the invention, the added weights along with the weight of the wedge rings 620 and 624 yield a total load of 5 kilograms.

Next, the cover 610 is visually inspected for seam puckers. The viewing direction and viewing angle should be adjusted as necessary to achieve the best perception of seam puckers. The number of perceivable seam puckers is then determined along with the length of each seam pucker.

Each seam may also be tested to determine the roughness of each seam. For example, the person conducting the test may lightly press a finger on the cover 610 and run his finger along the seams to feel the roughness of each seam. The person's finger should be approximately 90° with respect to the seam. Seam puckering may then be rated in any suitable manner, such as by using Table 6 shown below.

TABLE 6

Rating of Seam Puckers

| Observation / Evaluation | Rating |
| --- | --- |
| No visual pucker. Smooth seams | 5 |
| No visual pucker. Slightly rough seam | 4.5 |
| Visual pucker but hard to perceive in best view direction | 4 |
| Visual pucker easy to perceive in best view direction, pucker less than 5 mm long, # of puckers less than 3 | 3.5 |
| Visual pucker easy to perceive in all view directions, pucker less than 5 mm long, # of puckers less than 3 | 3 |
| Obvious pucker in all view directions, pucker less than 7 mm, # of puckers less than 5 | 2.5 |
| Obvious pucker in all view directions, pucker less than 7 mm, # of puckers less than 7 | 2 |
| Obvious pucker in all view directions, pucker less than 10 mm, # of puckers less than 7 | 1.5 |
| Obvious pucker in all view directions, pucker longer than 10 mm | 1 |

The method may also include determining a seam pucker requirement for a particular vehicle seat, and comparing the rating of the specimen 610 with the seam pucker requirement. For example, the seam pucker requirement for a particular vehicle seat may be set at a minimum of 3. In such a case, if the specimen 610 has a rating below 3, then the cover material from which the specimen 610 was cut will not be considered suitable for use with the particular vehicle seat.

The stretch standard provides a method for determining usability of a cover material as a seat cover of a vehicle seat or vehicle seat component, such as a seat bottom, seat back, armrest, headrest, or portion of any of the above elements, based on stretch characteristics. More specifically, the method of the stretch standard includes determining a fabric stretch requirement for the vehicle seat or vehicle seat component that will result in essentially no seat cover wrinkles due to stretch characteristics of the cover material. The method further includes determining actual fabric stretch of the cover material, and comparing the actual fabric stretch with the fabric stretch requirement to determine whether the cover material is satisfactory for use with the vehicle seat or vehicle seat component.

Figure 23:
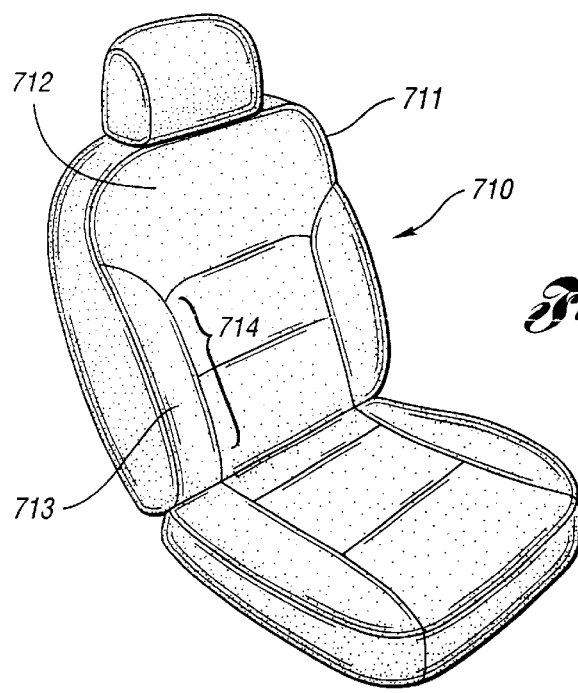
FIG. 23 is a perspective view of a virtual vehicle seat, having a vehicle seat contour, for use with a stretch standard of the invention.

Referring to FIG. 23, a more detailed description of the method of the stretch standard will now be provided. The method begins by obtaining a desired vehicle seat contour, which may also be referred to as final vehicle seat contour, of a vehicle seat 710 with which a proposed cover material is to be used as a seat cover or portion of the seat cover. This step may be accomplished in any suitable manner, such as by obtaining a virtual or electronic design of the vehicle seat contour, with or without a seat cover. Such an electronic design may be created, for example, by utilizing computer design software such as Unigraphics®, Alias®, Catia SDRC-IDEAS® and the like. Unigraphics® is available from Unigraphics Solutions, Inc. of Cypress, Calif.; Alias® is available from Alias Wavefront of Toronto, Ontario, Canada; and Catia SDRC-IDEAS® is available from International Business Machines Corporation of Armonk, N.Y. Furthermore, the vehicle seat contour preferably includes a component contour for each component of the vehicle seat 710.

Next, one or more conforming stretch requirements are determined for the vehicle seat 710 and associated vehicle seat contour, or for a component of the vehicle seat 710 and associated component contour. Conforming stretch requirements indicate the amount of stretch needed for a two-dimensional seat cover to conform to a three-dimensional shape of a vehicle seat contour with essentially no resultant wrinkles.

For a typical vehicle seat, a portion of the associated seat cover that covers a back bolster of the vehicle seat tends to require more stretch in order to conform to the vehicle seat contour than portions of the seat cover that cover other components or areas of the vehicle seat. This portion of the seat cover can be isolated as a panel, the boundary of which may be defined by seam lines such as sew lines. Within this panel, the center portion tends to bulge outwardly more than the boundary of the panel. As a result, the fabric near the center of the panel stretches more in order to conform to the vehicle seat contour. The fabric near the boundary, which typically is at a sew line or nearby a sew line, is either not stretched or only slightly stretched.

The three-dimensional contour of the panel can be seen as stretched out from a two-dimensional panel. A rectangular area or space within the panel can be further isolated with cross sections and work planes, as described below in detail. This rectangular area should cover the portion of the two-dimensional panel where no stretch, or very little stretch, is needed to conform to the corresponding three-dimensional contour. Furthermore, the rectangular area should also cover the portion of the two-dimensional panel that has to be stretched the greatest amount in order to conform to the corresponding three-dimensional contour. The boundary of the rectangular area along with the cross sections and work planes can be used to determine true line lengths, such as true arc lengths, of the three-dimensional contour at specific locations and directions. These true line lengths are stretched from the corresponding un-stretched lengths in the two-dimensional panel. The difference between the true line length and the un-stretched length at a specific location and direction may be used to determine a corresponding conforming stretch value. The highest conforming stretch value in a particular direction may be considered the conforming stretch requirement in the particular direction.

Figure 24:
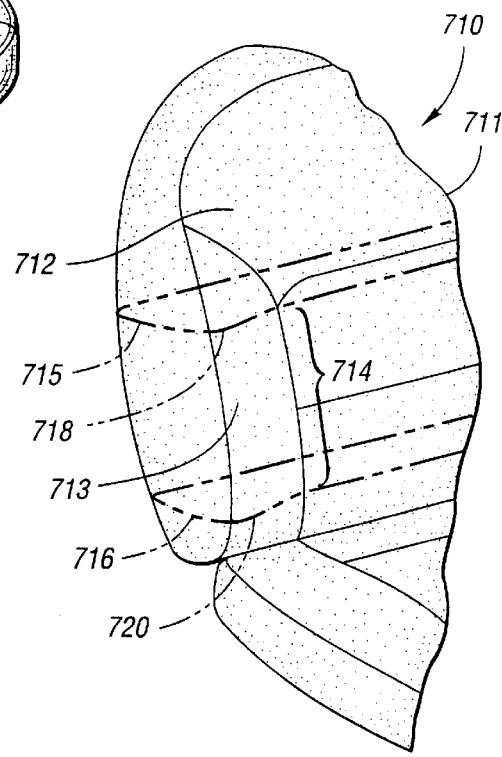
Figure 25:
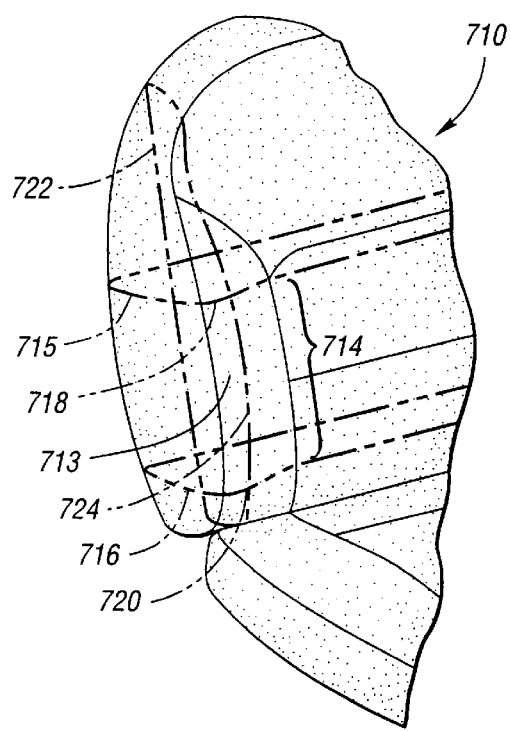
FIG. 25 is a fragmentary perspective view of the vehicle seat of FIG. 24 showing a cross-section cut through the vehicle seat, wherein the cross-section intersects a front surface of the vehicle seat back contour so as to define a surface line that extends between the work planes.

With reference to FIGS. 23–25, determination of a conforming stretch requirement in the up-down direction, for example, will now be described for seat back 711 of vehicle seat 710. It should be noted that FIGS. 23–25 represent an electronic design, such as a design developed using a computer, of vehicle seat 710, which includes a seat cover 712. Alternatively, determination of the conforming stretch requirement in the up-down direction, or other directions, may be accomplished using an electronic design of a body of vehicle seat 710, such as a foam core, without a seat cover. In such a case, the location of a seat cover may be approximated.

First, the component contour of seat back 711 is analyzed so as to select a surface portion, such as a panel 713 of seat cover 712, that appears to require the greatest amount of stretch. This step may be accomplished in any suitable manner, such as by visually inspecting the seat back 711. Next, the seam line or lines that encompass the panel 713, along with estimated back angle of a seat occupant, are determined. Estimated back angle may be determined, for example, through computer simulation.

A seam segment, such as a sew line segment 714, that extends in the up-down direction and that is generally straight or flat is then selected. Next, referring to FIG. 24, two parallel work planes 715 and 716 that are perpendicular to the estimated back angle are cut or otherwise established through the seat back 711 at opposite ends of the sew line segment 714, such that the work planes 715 and 716 intersect the panel 713 and define two boundary lines 718 and 720 that are disposed at opposite ends of the sew line segment 714. Preferably, the work planes 715 and 716 and associated boundary lines 718 and 720 are spaced as far apart as possible so that the conforming stretch requirement can be accurately determined. It should be noted that the work planes 715 and 716 may also be referred to as work lines.

Referring to FIG. 25, multiple cross sections, such as cross-car sections 24, are then cut or otherwise established through the seat back 711 such that the cross car sections 724 are perpendicular to the work planes 715 and 716 and intersect the panel 713 so as to define surface lines 724 extending between the boundary lines 718 and 720 (only one cross-car section 722 and corresponding surface line 724 are shown in FIG. 25). Typically, a spacing of about 15 millimeters between cross car sections 722 is recommended. However, spacing may be adjusted as needed for a particular application. For example, if a particular vehicle seat has a vehicle seat contour that includes significant curvature, then a closer spacing between cross car sections may be desirable.

Next, the length of each surface line 724 and the length of the sew line segment 714 are determined. The conforming stretch requirement (CS) in the up-down direction may then be determined using the following equation:

$$CS = \frac{\text{Longest surface line length} - \text{Sew line segment length}}{\text{Sew line segment length}} \times 100$$

If a generally straight or flat sew line segment, or other seam segment, cannot be located between the boundary lines 718 and 720, then the conforming stretch requirement in the up-down direction may be determined using the following equation:

$$CS = \frac{\text{Longest surface line lenth} - \text{Shortest surface line length}}{\text{Shortest surface line length}} \times 100$$

With either of the above equations, the conforming stretch requirement is determined as a percentage.

If multiple conforming stretch values are determined in the up-down direction for various portions of the seat back 711, then the largest conforming stretch value in the up-down direction may be established as the conforming stretch requirement for the entire seat back 711 in the up-down direction. Conforming stretch requirements for the seat back 711 may also be determined in other directions, such as a side—side direction or diagonal direction, using the process described above or a similar process. If different cover materials are to be used for different portions of the seat back 711, then conforming stretch requirements should be determined for each different portion.

Conforming stretch requirements for other components of the vehicle seat 710 may also be determined using the process described above or a similar process. If multiple conforming stretch values are determined in a particular direction for a particular component, then the largest conforming stretch value in the particular direction may be selected or otherwise established as the conforming stretch requirement in the particular direction for the particular component and associated component contour.

If the same cover material is to be used for the entire vehicle seat 710, then the largest conforming stretch value in a particular direction may be established as the conforming stretch requirement in that direction for the entire vehicle seat 710. Alternatively, if different cover materials are to be used for different components, then conforming stretch requirements for each of the components should be determined.

After the conforming stretch requirement or requirements have been determined, a classification for the vehicle seat contour or component contour may be determined using Table 7, which is shown below.

TABLE 7

| Requirement on Conforming Stretch | Seat/Component Contour (class) |
|---|---|
| CS ≦ 4% | Low |
| 4% < CS ≦ 10% | Medium |
| 10% < CS ≦ 12% | High |
| 12% < CS | Extra-high |

Table 7 provides an example of how vehicle seat contours or component contours may be classified based on conforming stretch requirements. For purposes of classification, the largest calculated conforming stretch requirement, regardless of direction, is used as the conforming stretch requirement for a particular vehicle seat contour or component contour. If, for instance, the maximum conforming stretch requirement for a particular vehicle seat contour falls between 4% and 10%, then the vehicle seat contour will be classified as a medium contour, according to Table 7. As another example, if the maximum conforming stretch requirement for a particular component contour, such as a headrest contour, falls between 10% and 12%, then the component contour will be classified as a high contour, according to Table 7. Alternatively, conforming stretch requirement ranges may be used to identify vehicle seat contour classifications or component contour classifications, without converting the ranges to verbal descriptions.

It should be noted that the conforming stretch requirements shown in Table 7 are determined based on configurations of vehicle seat contours, without regard to the amount of force necessary to conform seat covers to the vehicle seat contours. Furthermore, the conforming stretch requirements shown in Table 7 apply to all types of seat covers, regardless of the materials used in the manufacture of the seat covers.

Next, if the proposed cover material includes a foam sheet, thickness of the foam sheet is determined. Alternatively, if the proposed cover material does not yet include a foam sheet, but the particular vehicle seat application permits use of a foam sheet, then the anticipated thickness of the foam sheet may be determined or otherwise established.

Next, minimum and maximum fabric stretch requirements in various directions may be determined using a look-up table, such as Table 8 shown below for example.

TABLE 8

| Foam Sheet | Minimum stretch, % | | | | | Maximum stretch, % |
|---|---|---|---|---|---|---|
| Thickness, mm | ≦2 | 3–4 | 5–6 | 7–8 | ≧8 | All |
| Medium seat contour | | | | | | |
| Machine dir., % | 9 | 8 | 7 | 6 | 5 | 35 |
| Cross-machine dir., % | 9 | 8 | 7 | 6 | 5 | 35 |

TABLE 8-continued

| Foam Sheet | Minimum stretch, % | | | | | Maximum stretch, % |
|---|---|---|---|---|---|---|
| Thickness, mm | ≦2 | 3–4 | 5–6 | 7–8 | ≧8 | All |
| Diagonal, +45°, % | 14 | 12 | 12 | 11 | 11 | 35 |
| Diagonal, −45°, % | 14 | 12 | 12 | 11 | 11 | 35 |
| High seat contour | | | | | | |
| Machine dir., % | 11 | 10 | 9 | 8 | 7 | 35 |
| Cross-machine dir., % | 11 | 10 | 9 | 8 | 7 | 35 |
| Diagonal, +45°, % | 14 | 12 | 12 | 11 | 11 | 35 |
| Diagonal, −45°, % | 14 | 12 | 12 | 11 | 11 | 35 |

Table 8 provides fabric stretch requirements based on foam sheet thickness and vehicle seat contour classification or component contour classification, and the fabric stretch requirements indicate the stretch characteristics a particular cover material should have in order for the cover material to be able to conform to a particular vehicle seat contour or component contour with essentially no wrinkles due to stretch characteristics. Furthermore, Table 8 provides fabric stretch requirements in the machine direction, cross-machine direction and diagonal directions. The machine direction is the direction in the plane of a cover material parallel to the direction of manufacture, the cross-machine direction is the direction in the plane of a cover material perpendicular to the direction of manufacture, and diagonal directions are directions in the plane of a cover material extending at specified angles from the machine direction. For woven fabrics, the machine direction is known as warp direction and the cross-machine direction is known as fill direction. For knit fabrics, the machine direction is known as wale direction and the cross-machine direction is known as course direction. However, for knit fabrics, warp is frequently used in place of wale, and fill is used in place of course.

The fabric stretch requirements shown in Table 8 are based on extensive testing of various fabric cover materials with various vehicle seat contours and/or component contours. Under one test procedure, for example, a square grid is established on a particular cover material, and the cover material is then stretched so as to conform the cover material to a particular vehicle seat contour. Changes in spacing of points and/or lines of the grid are then noted in the machine direction, cross-machine direction, +45° diagonal direction and −45° diagonal direction. Next, fabric conforming stretch requirements are determined in each of these directions based on the changes in the grid.

A conforming force corresponding to each fabric conforming stretch requirement is then determined using any suitable approach. For example, strips having suitable dimensions, such as 25.4 mm×101.6 mm, and extending in various directions may be marked on the cover material when the cover material is stretched over the particular vehicle seat contour. The long sides of each strip are then cut through the thickness of the cover material. Next, each strip is cut in the middle along a direction parallel to the short sides of the strip so as to form two strip pieces. Because of the reduction in tensile forces, the strip pieces of each strip shrink in length as compared with the corresponding uncut strip. A force is then applied to one strip piece of each strip so as to stretch the strip piece back to its original position. This force is referred to as the conforming force. Each fabric conforming stretch requirement may then be referred to as a fabric stretch requirement at the corresponding conforming force. Each fabric stretch requirement at the corresponding conforming force is then correlated to a fabric stretch requirement at a 50 Newton stretch force applied over a width of approximately 25.4 mm so as to establish the fabric stretch requirements shown in Table 8. Numerous tests with various fabrics may be performed in order to establish the correlation between the fabric stretch requirements at corresponding conforming forces and the fabric stretch requirements at a 50 Newton stretch force. Thus, all of the fabric stretch requirements shown in Table 8 are based on application of a 50 Newton stretch force over a cover material width of approximately 25.4 mm. Alternatively, a table may be developed or otherwise provided with fabric stretch requirements based on a smaller or larger stretch force that is applied over a smaller or larger cover material width.

The maximum fabric stretch requirement shown in Table 8 provides an upper limit on fabric stretch values. It has been found that cover materials having fabric stretch values above this limit tend to be unstable during cover manufacturing processes, such as cut and sew operations.

As an example of how to utilize Table 8, fabric stretch requirements for a proposed cover material having a 3 millimeter thick foam sheet will now be determined. In order for such a cover material to be useable with a vehicle seat having a medium contour classification, or a vehicle seat component having a medium contour classification, the cover material should have a machine direction fabric stretch between 8% and 35%, a cross-machine fabric stretch between 8% and 35%, a +45° diagonal fabric stretch between 12% and 35%, and a −45° diagonal fabric stretch between 12% and 35%, according to Table 8. If no seat contour classification has been determined, medium seat contour classification may be assumed.

Next, actual fabric stretch values are determined for the proposed cover material. For example, one or more specimens of the proposed cover material may be tested according to ASTM D 5034-95, Standard Test Method for Breaking Strength and Elongation of Textile Fabrics (Grab Test), in order to determine actual machine direction fabric stretch, actual cross-machine fabric stretch, actual +45° diagonal stretch, and actual −45° diagonal fabric stretch. The percent elongation in a particular direction of a particular specimen at a 50 Newton stretch force, or other force that is consistent with the force on which the fabric stretch requirements are based, may be considered the actual fabric stretch value for the particular direction.

Next, the actual fabric stretch values are compared with the fabric stretch requirements. If all of the actual fabric stretch values fall within the corresponding fabric stretch requirement ranges, then the proposed cover material is considered useable as a seat cover, based on stretch characteristics, for vehicle seat 710, or a specific component of vehicle seat 710, depending on whether the above process was carried out for the entire vehicle seat 710 or a specific component, such as seat back 711, of vehicle seat 710. If any one of the fabric stretch values falls below the corresponding minimum fabric stretch requirement, then the proposed cover material will likely exhibit excessive wrinkling and/or tearing if it is used with the vehicle seat 710. If any one of the fabric stretch values falls above the corresponding maximum fabric stretch requirement, then the proposed cover material will likely cause difficulties for cut and sew operations.

The elongation standard provides a method for determining usability of a cover material as a seat cover for a particular vehicle seat application based on elongation characteristics. During seat back assembly, for example, a seat back cover is stretched and inverted to fit onto a seat back, which includes a seat back frame and foam pad. The cover is often in the form of a bag having a cover opening. To fit the cover over the frame and foam pad, the cover opening is expanded in order to slide over mid sections of the seat back that are often wider than the cover opening. Advantageously, the elongation standard provides an elongation requirement for such a cover so as to minimize the risk of tearing.

The method of the elongation standard may include determining circumferences of various mid sections or cross sections of a proposed seat back in order to determine the amount of extension or expansion required at a cover opening of a seat back cover. For example, such circumferences may be obtained from an electronic design, such as a computer model, of the seat back. Using the electronic design, cross sections through the seat back and normal to the estimated back angle, which is described above with respect to the stretch standard, may be determined by cutting or otherwise establishing work planes through the seat back. Such work planes, which may also be referred to as work lines, are similar to the work planes described above with respect to the stretch standard, and each work plane defines a cross section extending through the entire seat back. A circumference is then determined for each cross section.

If the electronic design does not include a seat back cover, then envelopes that encompass the cross sections should first be established. For each cross section, the corresponding envelope approximates the location of a seat back cover. A circumference is then determined for each envelope.

Next, the largest circumference of the seat back and the circumference of the cover opening are used to determine the amount of extension or expansion required at the cover opening. The smallest circumference of the seat back may be used as the circumference of the cover opening. For example, the following equation may be used to determine the percentage of expansion required at the cover opening ($EP_o$):

$$EPo = \frac{Lmax - Lmin}{Lmin} \times 100,$$

where $L_{max}$ is the circumference of the largest cross section or envelope, and $L_{min}$ is the circumference of the smallest cross-section or envelope.

In general, the percentage of expansion of the cover opening ($EP_0$) can be linked to the risk of tearing covers during seat back cover inversion processes. For example, Table 9, which is shown below, may be used to assign tearing risk of a seat back design based on the expansion of the cover opening.

TABLE 9

Expansion of Cover Opening vs. Risk of Tearing Cover

| Expansion of Cover Opening | Risk of Tearing Cover |
|---|---|
| $EPo \leq 15\%$ | Low |
| $15\% < EPo \leq 25\%$ | Medium |
| $25\% < EPo \leq 35\%$ | High |
| $35\% < EPo$ | Extra-high |

Generally, it is desirable to design seats such that the expansion of the cover opening does not exceed 25%.

Other factors, such as a map pocket of the cover, the design of seams of the cover, and the location of J-clips that attach the cover to the seat back frame, may also be considered in a mechanical model, which may be used to calculate the elongation of the cover at various locations along the cover opening when the cover opening is expanded. Advantageously, the mechanical model accounts for different elongation characteristics at different locations along the opening of the cover. For example, if the back portion of the cover is to be provided with a map pocket, then the back portion will likely not stretch as much as side portions of the cover during a seat back cover inversion process. As a result, the back portion, or a section of the back portion, may be represented as two springs in parallel (one spring for the cover material, and one spring for the map pocket). Similarly, because the front portion of the cover may be provided with additional foam thickness, as compared with the side portions, the front portion, or a section of the front portion, may be represented as two springs in parallel. The entire cover opening may then be represented as two parallel back springs in series with one or more right side springs, two parallel front springs, and one or more left side springs.

Figure 26:
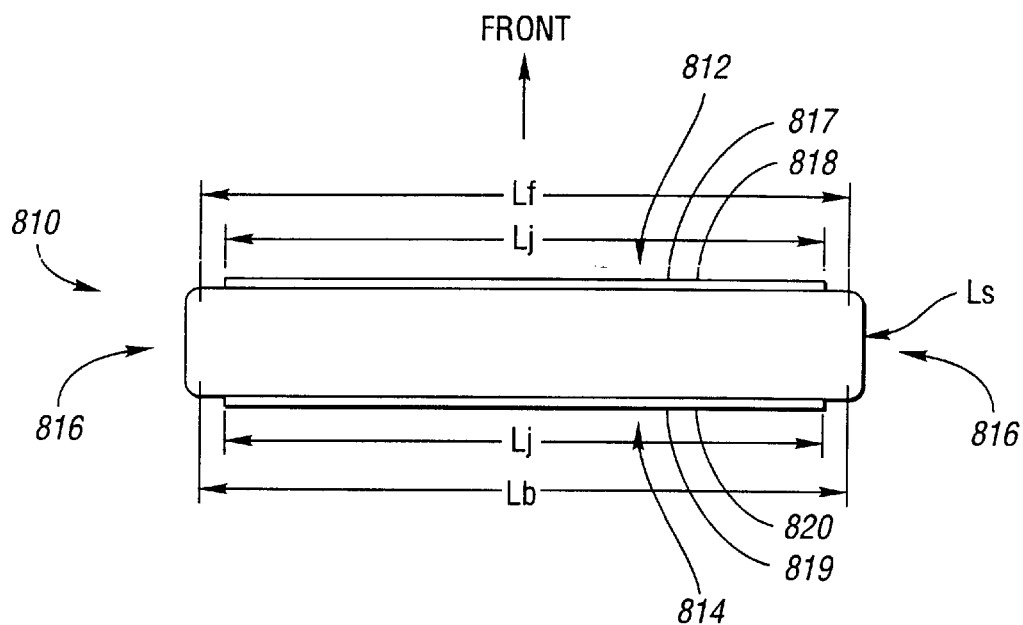
FIG. 26 shows a schematic of a seat cover opening for use with an elongation standard of the invention.
Figure 27:
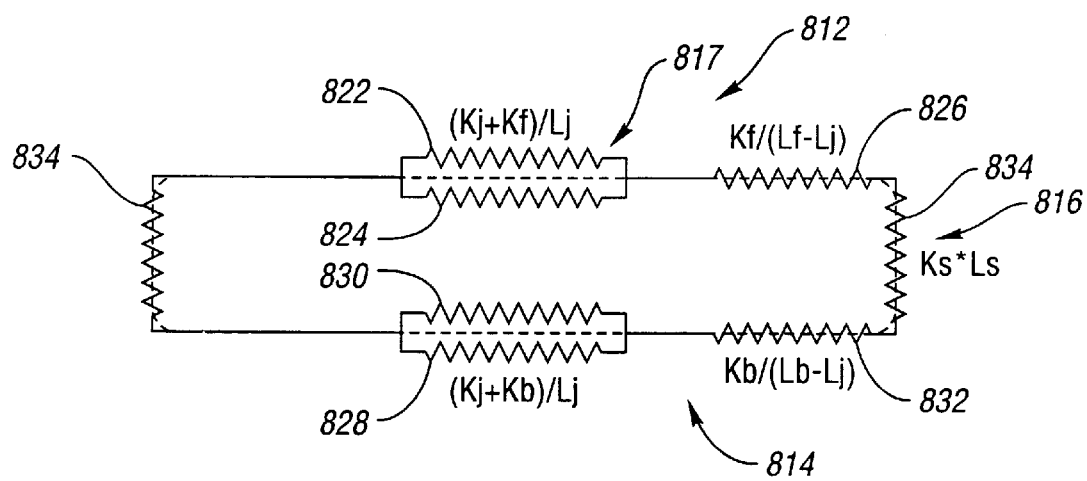
FIG. 27 shows a mechanical model of the seat cover opening of FIG. 26.

Referring to FIGS. 26 and 27, a more detailed example involving use of a mechanical model will now be provided. FIG. 26 shows a schematic view of a seat cover opening 810 made of a particular cover material or materials. The cover opening 810 includes a front portion 812, a back portion 814, and two side portions 816. The front portion 812 has an overall length $L_f$, and includes a first section 817 having a first seat back frame attachment system 818 attached thereto. The first frame attachment system 818 may include, for example, a J-clip and additional material, such as fabric, sewn to the J-clip. The back portion 814 has an overall length $L_b$, and includes a second section 819 having a second seat back frame attachment system 820. In this example, the first and second sections 817 and 819, respectively, each have an overall length $L_j$. However, the sections 817 and 819 may have different lengths. The second section 819 may also include a map pocket (not shown).

FIG. 27 shows a mechanical model of the seat cover opening 810. The first section 817 of the front portion 812 is represented as first and second front springs 822 and 824, respectively, in parallel. The first front spring 822 represents the cover material or materials used to make the front portion 812, and the second front spring 824 represents the frame attachment system 818. The remainder of the front portion 812 is represented as a third front spring 826 in series with the parallel first and second front springs 822 and 824, respectively. The second section 819 of the back portion 814 is represented as first and second back springs 828 and 830, respectively, in parallel. The first back spring 828 represents the cover material or materials used to make the back portion 814, and the second back spring 830 represents the second frame attachment system 820. The first back spring 828 may also represent a map pocket if applicable. The remainder of the back portion 814 is represented as a third back spring 832 in series with the parallel first and second back springs 828 and 830, respectively. Each side portion 816 is represented as a side spring 834.

The total elongation $L_t$ for the seat cover opening 810 during a seat back cover inversion process may be represented by the following equation:

$$L_t = (F/K_t) \times (L_f + L_b + 2L_s) = (F/(K_f + K_j)) \times L_j + (F/K_f) \times (L_f - L_j) + (F/K_s) \times 2L_s + (F/(K_f + K_b)) \times L_j + (F/K_b) \times (L_b - L_1),$$

where F is the load along seat cover opening 810 during the seat back cover inversion process, $K_t$ is the total spring constant for the seat cover opening 810, $K_j$ is the spring constant for each of the frame attachment systems 818 and 820, $K_f$ is the spring constant of the cover material or materials along front portion 812, $K_b$ is the spring constant of the cover material or materials along the back portion 814, and $K_s$ is the spring constant of the cover material or materials along each of the side portions 816. In this example, each frame attachment system 818 and 820 has the same spring constant. The first frame attachment system 818 may, however, have a different spring constant than the second frame attachment system 820.

Each spring constant identified in the above equation may be defined as the load applied to a particular material divided by the corresponding elongation of a unit length of the material. Furthermore, each spring constant may vary with the load applied to the material.

From the above equation, the inverse of the total spring constant $K_t$ may be represented by the following equation:

$$1/K_t=[(1/(K_j+K_f))\times L_f+(1/K_f)\times(L_f-L_j)+(1/K_s)\times 2L_s+(1/(K_j+K_b))\times L_j+(1/K_b)\times(L_b-L_j)]/(L_f+L_b+2L_s)$$

The spring constants $K_f$, $K_b$, and $K_s$ may be obtained by conducting elongation tests of the cover material or materials. The spring constant $K_j$ may be obtained by conducting elongation tests on one or both of the frame attachment systems 818 and 820. The total elongation $L_t$ is determined by seat design and set up of an inverter for use in the seat back cover inversion process. The load F along the seat cover opening 810 may then be solved by using the following equation:

$$F=L_t\times K_t/(L_f+L_b+2L_s)$$

Elongation percentages for the various portions 812, 814 and 816 of the seat cover opening 810 may then be determined by the following equations:

Elongation % for section 817: $E_{fj}=F/(K_j+K_f)\times 100$;

Elongation % for remainder of front portion 812: $E_f=(F/K_f)\times 100$;

Elongation % for section 819: $E_{bj}=F/(K_j+K_b)\times 100$;

Elongation % for remainder of back portion 814: $E_b=(F/K_b)\times 100$; and Elongation % for side portion 816: $E_s=(F/K_s)\times 100$ The expansion of the cover opening, the mechanical model and associated elongation percentages, and the historical performance of fabrics, such as elongation test results and performance characteristics during seat back inversion processes, may then be used to derive a requirement on the elongation at breakage for cover materials to be used as seat covers. A minimum elongation at breakage of 35% in each of the machine direction and cross-machine direction is generally satisfactory for the majority of seats. A specific elongation at breakage requirement for a particular seat may also be determined using the above process, based on the design of the seat and the design of the cover.

The actual elongation at breakage of the proposed cover material is then determined. For example, a suitable tensile force may be applied to a specimen of the cover material so as to stretch the specimen to a point where the specimen breaks. If the actual elongation at breakage is equal to or greater than 35%, and if the expansion of the cover opening does not exceed 25% for the proposed seat back, then the cover material should be acceptable for use as a cover for the seat back.

One or more of the above described standards may be used to select a sufficiently processable cover material for use as a seat cover for a particular vehicle seat application. Generally, then, a method according to the invention for selecting a cover material for use with a vehicle seat component, such as a seat bottom, seat back, armrest, headrest, or portion of any of the above elements, includes establishing a material processability standard for cover materials selected from the group consisting of standards for marking resistance, fabric pattern, pile bind, rippling resistance, laminate wrinkle resistance, raveling resistance, seam puckering, stretch, and elongation. Establishing such a standard may include creating or otherwise developing the standard, or simply determining that an already developed standard is acceptable for use with a particular vehicle seat application.

The method includes conducting testing of a cover material for compliance with the standard to determine whether the cover material meets requirements of the standard. Test results of the cover material may then be considered before proceeding to utilize the cover material in manufacturing of the vehicle seat component. This step may also include conferring with a vehicle manufacturer regarding the test results and/or the standard when the cover material does not meet the requirements of the standard. As a result, all interested parties may be involved in selecting a suitable cover material before proceeding to utilize the cover material in the manufacturing process.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for determining usability of a cover material with a vehicle seat component, the method comprising:
   establishing a laminate wrinkle resistance material processability standard for cover materials, wherein the material processability standard is for use in determining the ability of the cover material to be processed as a cover of the vehicle seat component;
   conducting testing of the cover material for compliance with the material processability standard to determine whether the cover material meets requirements of the material processability standard; and
   considering test results of the cover material before proceeding to utilize the cover material in manufacturing of the vehicle seat component.

2. The method of claim 1 further comprising establishing a marking resistance material processability standard and conducting testing of the cover material for compliance with the marking resistance standard, wherein the step of conducting testing for compliance with the marking resistance standard includes brushing a first portion of a specimen of the cover material in a first direction, and determining a contrast level for the first portion and a second portion of the specimen.

3. The method of claim 1 further comprising establishing a marking resistance material processability standard and conducting testing of the cover material for compliance with the marking resistance standard, wherein the step of conducting testing for compliance with the marking resistance standard includes brushing first and second portions of a specimen of the cover material in a first direction, brushing the first portion in a second direction different than the first direction, and determining a contrast level for the first and second portions.

4. The method of claim 3 wherein the step of establishing a marking resistance standard includes determining a marking resistance requirement, and wherein the step of conducting testing for compliance with the marking resistance standard further includes comparing the contrast level to the marking resistance requirement.

5. The method of claim 1 further comprising establishing a fabric pattern material processability standard and conducting testing of the cover material for compliance with the fabric pattern standard, wherein the step, of conducting testing for compliance with the fabric pattern standard includes examining a specimen of the cover material so as to identify a generally straight line formed by a characteristic of the cover material, and determining a line angle of the line with respect to a direction of the specimen.

6. The method of claim 5 wherein the step of establishing a fabric pattern standard includes establishing a first line angle limit and a second line angle limit greater than the first line angle limit, and wherein the step of conducting testing for compliance with the fabric pattern standard further includes comparing the line angle to the line angle limits, and determining a width of the line if the line angle does not fall between the line angle limits.

7. The method of claim 6 wherein the step of conducting testing for compliance with the fabric pattern standard further includes determining a contrast level for the line if the line angle does not fall between the line angle limits.

8. The method of claim 1 further comprising establishing a fabric pattern material processability standard and conducting testing of the cover material for compliance with the fabric pattern standard, wherein the step of conducting testing for compliance with the fabric pattern standard includes examining a specimen of the cover material so as to identify any generally straight lines formed by a characteristic of the cover material, determining a line angle with respect to a cross-machine direction of the specimen for each line identified, determining a line width for each line identified if the corresponding line angle falls outside a predetermined angle range, determining a contrast level for each line identified if the corresponding line angle falls outside the predetermined angle range, determining a rating for the specimen based on the line width and the contrast level of at least one line if any lines are identified, and comparing the rating with a predetermined fabric pattern rating requirement.

9. The method of claim 1 further comprising establishing a pile bind material processability standard and conducting testing of the cover material for compliance with the pile bind standard, wherein the step of conducting testing for compliance with the pile bind standard includes subjecting a back surface of a specimen of the cover material to an abrasive member, and then examining the specimen to detect holes caused by loss of pile tufts.

10. The method of claim 9 wherein the step of establishing a pile bind standard includes establishing a pile bind requirement, and wherein the step of conducting testing for compliance with the pile bind standard includes determining a pile loss value for the specimen based on the number of holes, if any, detected, and comparing the pile loss value to the pile bind requirement.

11. The method of claim 1 further comprising establishing a rippling resistance material processability standard and conducting testing of the cover material for compliance with the rippling resistance standard, wherein the step of conducting testing for compliance with the rippling resistance standard includes applying a tensile force to a specimen of the cover material, examining the specimen to detect wrinkles, and measuring depth of the deepest wrinkle detected, if any.

12. The method of claim 11 wherein the step of establishing a rippling resistance standard includes establishing a rippling resistance rating requirement, and wherein the step of conducting testing for compliance with the rippling resistance standard includes determining a rippling resistance rating for the specimen based on the depth of the deepest wrinkle detected, if any, and comparing the rippling resistance rating to the rippling resistance rating requirement.

13. The method of claim 1 wherein the step of conducting testing includes applying a load to a specimen of the cover material using a movable member so as to cause the specimen to bend, and examining the specimen to detect wrinkles.

14. The method of claim 13 wherein the step of conducting testing includes determining a thickness (T) of the specimen, determining a displacement (D) of the movable member from a first position to a second position where a wrinkle first appears, and determining a wrinkle resistance index (WRI) using the following equation:

$$WRI = 0.16 \times (T+D) + 0.01 \times (T+D)^2.$$

15. The method of claim 14 wherein the step of establishing a laminate wrinkle resistance material processability standard includes establishing a wrinkle resistance requirement, and wherein the step of conducting testing further includes comparing the WRI to the wrinkle resistance requirement.

16. The method of claim 1 further comprising establishing a raveling resistance material processability standard and conducting testing of the cover material for compliance with the raveling resistance standard, wherein the step of conducting testing for compliance with the raveling resistance standard includes cutting a specimen of the cover material so as to form first and second portions, blowing air onto the second portion so as to cause the second portion to flap, and comparing the second portion to the first portion to determine how many yarns, if any, of the second portion became raveled as a result of blowing air onto the second portion.

17. The method of claim 1 farther comprising establishing a raveling resistance material processability standard and conducting testing of the cover material for compliance with the raveling resistance standard, wherein the step of conducting testing for compliance with the raveling resistance standard includes cutting a specimen of the cover material along first and second lines so as to form first and second flap portions and a middle portion disposed between the flap portions, blowing air onto the middle portion so as to cause the middle portion to move up and down, examining the middle portion to determine along which of the first and second lines more yarns of the middle portion became raveled as a result of blowing air onto the middle portion, removing yarns from one of the flap portions that is adjacent to the line along which more yarns of the middle portion became raveled until yarns of the one flap portion are aligned with non-raveled yarns of the middle portion, and determining the number of yarns removed from the one flap portion.

18. The method of claim 1 further comprising establishing a seam puckering material processability standard and conducting testing of the cover material for compliance with the seam puckering standard, wherein the step of conducting testing for compliance with the seam puckering standard includes cutting panels from the cover material, sewing the panels together to form a cover having seams, positioning the cover on a form such that a first portion of the cover extends to an inner ring that is disposed beneath the form and movable with respect to the form, positioning an outer ring over the cover such that the first portion is sandwiched between the inner and outer rings, applying a load to the outer ring so as to apply a tensile load to the cover, and examining the cover to detect seam puckers, if any.

19. The method of claim 1 further comprising establishing an elongation material processability standard that includes an elongation at breakage requirement, and conducting testing of the cover material for compliance with the elongation standard, wherein the step of conducting testing for compliance with the elongation standard includes determining an elongation at breakage of the cover material, and comparing the elongation at breakage with the elongation at breakage requirement.

20. The method of claim 19 wherein the step of establishing the elongation standard includes establishing the elongation at breakage requirement based on an elongation percentage derived from a mechanical model of a seat cover opening.

21. The method of claim 19 wherein the step of establishing the elongation standard includes establishing the elongation at breakage requirement based on a cover opening percentage of expansion derived from an electronic design of a seat back.

22. The method of claim 1 wherein the step of considering test results includes conferring with a vehicle manufacturer regarding the test results when the cover material does not meet the requirements of the material processability standard.

23. The method of claim 1 further comprising:
    establishing an additional material processability standard selected from the group consisting of standards for marking resistance, fabric pattern, pile bind, rippling resistance, laminate wrinkle resistance, raveling resistance, seam puckering, stretch, and elongation;
    conducting testing of the cover material for compliance with the additional material processability standard to determine whether the cover material meets requirements of the additional material processability standard; and
    considering additional test results of the cover material for the additional material processability standard tested before proceeding to utilize the cover material in manufacturing of the vehicle seat component.

24. The method of claim 23 wherein the step of considering additional test results includes conferring with the vehicle manufacturer regarding the additional test results when the cover material does not meet the requirements of the additional material processability standard.

25. A method for determining usability of a cover material with a vehicle seat component, the method comprising:
    establishing a laminate wrinkle resistance material processability standard and an additional material processability standard selected from the group consisting of standards for marking resistance, fabric pattern, pile bind, rippling resistance, raveling resistance, seam puckering, stretch, and elongation;
    conducting testing of the cover material for compliance with each of the established material processability standards to determine whether the cover material meets requirements of each established material processability standard; and
    considering test results of the cover material for each established material processability standard tested before proceeding to utilize the cover material in manufacturing of the vehicle seat component.

26. A method for determining usability of a cover material with a vehicle seat component, the method comprising:
    conducting testing of the cover material for compliance with a laminate wrinkle resistance material processability standard and an additional material processability standard selected from the group consisting of standards for marking resistance, fabric pattern, pile bind, rippling resistance, raveling resistance, seam puckering, stretch, and elongation to determine whether the cover material meets requirements of the laminate wrinkle resistance material processability standard and the additional material processability standard before proceeding to utilize the cover material in manufacturing of the vehicle seat component.

27. The method of claim 26 wherein the step of conducting testing for compliance with the additional material processability standard is performed in accordance with a marking resistance standard and includes brushing a first portion of a specimen of the cover material in a first direction, and determining a contrast level for the first portion and a second portion of the specimen.

28. The method of claim 26 wherein the step of conducting testing for compliance with the additional material processability standard is performed in accordance with a marking resistance standard and includes brushing first and second portions of a specimen of the cover material in a first direction, brushing the first portion in a second direction different than the first direction, and determining a contrast level for the first and second portions.

29. The method of claim 28 wherein the step of conducting testing for compliance with the additional material processability standard further includes comparing the contrast level of the specimen to a marking resistance requirement of the marking resistance standard.

30. The method of claim 26 wherein the step of conducting testing for compliance with the additional material processability standard is performed in accordance with a fabric pattern standard and includes examining a specimen of the cover material so as to identify a generally straight line formed by a characteristic of the cover material, and determining a line angle of the line with respect to a direction of the specimen.

31. The method of claim 30 wherein the step of conducting testing for compliance with the additional material processability standard further includes comparing the line angle to a predetermined angle range, and determining a width of the line if the line angle falls outside of the predetermined angle range.

32. The method of claim 31 wherein the step of conducting testing for compliance with the additional material processability standard further includes determining a contrast level for the line if the line angle falls outside the predetermined angle range.

33. The method of claim 26 wherein the step of conducting testing for compliance with the additional material processability standard is performed in accordance with a fabric pattern standard and includes examining a specimen of the cover material so as to identify any generally straight lines formed by a characteristic of the cover material, determining a line angle with respect to a cross-machine direction of the specimen for each line identified, determining a line width for each line identified if the corresponding line angle falls outside a predetermined angle range, determining a contrast level for each line identified if the corresponding line angle falls outside the predetermined angle range, determining a rating for the specimen based on the line width and the contrast level of at least one line if any lines are identified, and comparing the rating with a predetermined fabric pattern rating requirement.

34. The method of claim 26 wherein the step of conducting testing for compliance with the additional material processability standard is performed in accordance with a pile bind standard and includes subjecting a back surface of a specimen of the cover material to an abrasive member, and then examining the specimen to detect holes caused by loss of pile tufts.

35. The method of claim 34 wherein the step of conducting testing for compliance with the additional material processability standard includes determining a pile loss value for the specimen based on the number of holes, if any, detected, and comparing the pile loss value to a pile bind requirement of the pile bind standard.

36. The method of claim 26 wherein the step of conducting testing for compliance with the additional material processability standard is performed in accordance with a rippling resistance standard and includes applying a tensile force to a specimen of the cover material, examining the specimen to detect wrinkles, and measuring depth of the deepest wrinkle detected, if any.

37. The method of claim 36 wherein the step of conducting testing for compliance with the additional material processability standard includes determining a rippling resistance rating for the specimen based on the depth of the deepest wrinkle detected, if any, and comparing the rippling resistance rating to a rippling resistance rating requirement of the rippling resistance standard.

38. The method of claim 26 wherein the step of conducting testing for compliance with the laminate wrinkle resistance material processability standard includes applying a load to a specimen of the cover material using a movable member so as to cause the specimen to bend, and examining the specimen to detect wrinkles.

39. The method of claim 38 wherein the step of conducting testing for compliance with the laminate wrinkle resistance material processability standard includes determining a thickness (T) of the specimen, determining a displacement (D) of the movable member from a first position to a second position where a wrinkle first appears, and determining a wrinkle resistance index (WRI) using the following equation:

$$WRI=0.16\times(T+D)+0.01\times(T+D)^2.$$

40. The method of claim 39 wherein the step of conducting testing for compliance with the laminate wrinkle resistance material processability standard further includes comparing the WRI to a wrinkle resistance requirement of the laminate wrinkle resistance material processability standard.

41. The method of claim 26 wherein the step of conducting testing for compliance with the additional material processability standard is performed in accordance with a raveling resistance standard and includes cutting a specimen of the cover material so as to form first and second portions, blowing air onto the second portion so as to cause the second portion to flap, and comparing the second portion to the first portion to determine how many yarns, if any, of the second portion became raveled as a result of blowing air onto the second portion.

42. The method of claim 26 wherein the step of conducting testing for compliance with the additional material processability standard is performed in accordance with a raveling resistance standard and includes cutting a specimen of the cover material along first and second lines so as to form first and second flap portions and a middle portion disposed between the flap portions, blowing air onto the middle portion so as to cause the middle portion to move up and down, examining the middle portion to determine along which of the first and second lines more yarns of the middle portion became raveled as a result of blowing air onto the middle portion, removing yarns from one of the flap portions that is adjacent to the line along which more yarns of the middle portion became raveled until yarns of the one flap portion are aligned with non-raveled yarns of the middle portion, and determining the number of yarns removed from the one flap portion.

43. The method of claim 26 wherein the step of conducting testing for compliance with the additional material processability standard is performed in accordance with a seam puckering standard and includes cutting panels from the cover material, sewing the panels together to form a cover having seams, positioning the cover on a form such that a first portion of the cover extends to an inner ring that is disposed beneath the form and movable with respect to the form, positioning an outer ring over the cover such that the first portion is sandwiched between the inner and outer rings, applying a load to the outer ring so as to apply a tensile load to the cover, and examining the cover to detect seam puckers, if any.

44. The method of claim 26 wherein the step of conducting testing for compliance with the additional material processability standard is performed in accordance with an elongation standard and includes determining an elongation at breakage of the cover material, and comparing the elongation at breakage with an elongation at breakage requirement of the elongation standard.

45. The method of claim 44 wherein the elongation at breakage requirement is based on an elongation percentage derived from a mechanical model of a seat cover opening.

46. The method of claim 44 wherein the elongation at breakage requirement is based on a cover opening percentage of expansion derived from an electronic design of a seat back.

47. The method of claim 26 further comprising conferring with a vehicle manufacturer regarding test results of the cover material when the cover material does not meet requirements of the laminate wrinkle resistance material processability standard or the additional material processability standard.

48. The method of claim 26 wherein the step of conducting testing for compliance with the additional material processability standard includes conducting testing of the cover material for compliance with multiple additional material processability standards selected from the group consisting of standards for marking resistance, fabric pattern, pile bind, rippling resistance, raveling resistance, seam puckering, stretch, and elongation to determine whether the cover material meets requirements of the multiple additional material processability standards before proceeding to utilize the cover material in manufacturing of the vehicle seat component.

49. The method of claim 48 further comprising conferring with a vehicle manufacturer regarding test results of the cover material when the cover material does not meet requirements of at least one of the multiple additional material processability standards.

50. A method for determining usability of a cover material with a vehicle seat component, the method comprising:
   conducting testing of the cover material for compliance with a laminate wrinkle resistance material processability standard to determine whether the cover material meets a requirement of the material processability standard, wherein the step of conducting testing includes applying a load to a specimen of the cover material using a movable member so as to cause the specimen to bend, examining the specimen to detect wrinkles, determining a thickness (T) of the specimen, determining a displacement (D) of the movable member from a first position to a second position where a wrinkle first appears, and determining a wrinkle resistance index (WRI) using the following equation:

$$WRI = 0.16 \times (T+D) + 0.01 \times (T+D)^2.$$

51. The method of claim 50 wherein the step of conducting testing further includes comparing the WRI to a wrinkle resistance requirement of the material processability standard.

52. A method for determining usability of a cover material with a vehicle seat component, the method comprising:

conducting testing of the cover material for compliance with a laminate wrinkle resistance material processability standard to determine whether the cover material meets a requirement of the material processability standard, wherein the step of conducting testing includes applying a load to a specimen of the cover material using a movable member so as to cause the specimen to bend, examining the specimen to detect wrinkles, and determining a wrinkle resistance index based on thickness of the specimen and displacement of the movable member.

53. The method of claim 52 wherein the step of conducting testing further includes comparing the wrinkle resistance index to a wrinkle resistance requirement of the material processability standard.

54. The method of claim 52 wherein the step of conducting testing further includes supporting the specimen on two support elements, and wherein the step of applying a load comprises applying the load to the specimen in a direction that extends between the support elements using at least one load element supported by the movable member.

* * * * *

UNITED STATES PATENT AND TRADEMARK OFFICE
CERTIFICATE OF CORRECTION

PATENT NO.    : 6,609,408 B2
DATED         : August 26, 2003
INVENTOR(S)   : Pusheng Chen et al.

It is certified that error appears in the above-identified patent and that said Letters Patent is hereby corrected as shown below:

<u>Column 25,</u>
Line 8, after "step" delete the comma ",".

<u>Column 26,</u>
Line 40, delete "farther" and insert therefor -- further --.

Signed and Sealed this

Twenty-fourth Day of February, 2004

JON W. DUDAS
*Acting Director of the United States Patent and Trademark Office*